United States Patent [19]
Pierce

[11] Patent Number: 5,773,283
[45] Date of Patent: Jun. 30, 1998

[54] SYSTEMS AND METHODS FOR BIODEGRADATION

[75] Inventor: George E. Pierce, Lebanon, N.J.

[73] Assignee: Cytec Technology Corporation, Wilmington, Del.

[21] Appl. No.: 573,049

[22] Filed: Dec. 15, 1995

Related U.S. Application Data

[63] Continuation-in-part of Ser. No. 357,822, Dec. 16, 1994, Pat. No. 5,688,685, Ser. No. 357,686, Dec. 16, 1994, Pat. No. 5,633,164, Ser. No. 357,700, Dec. 16, 1994, Pat. No. 5,585,272, and Ser. No. 357,821, Dec. 16, 1994, Pat. No. 5,571,705.

[51] Int. Cl.$^6$ .................................. B09B 3/00; C02F 3/02
[52] U.S. Cl. ....................... 435/262; 435/262.5; 435/248; 210/627
[58] Field of Search ...................................... 535/262, 248, 535/253.3, 262.5, 264, 266, 174; 210/610, 611, 626, 627

[56] References Cited

U.S. PATENT DOCUMENTS

| | | |
|---|---|---|
| 3,779,866 | 12/1973 | Azarowicz . |
| 3,847,803 | 11/1974 | Fisk . |
| 4,249,929 | 2/1981 | Kneer . |
| 4,292,325 | 9/1981 | Coulthard et al. . |
| 4,385,121 | 5/1983 | Knowlton ................................ 435/244 |
| 4,492,756 | 1/1985 | Ghisalba et al. . |
| 4,493,895 | 1/1985 | Colaruotolo et al. . |
| 4,713,343 | 12/1987 | Wilson et al. . |
| 4,803,166 | 2/1989 | Kulpa et al. . |
| 4,843,007 | 6/1989 | Bedard et al. . |
| 4,876,201 | 10/1989 | Bedard et al. . |
| 5,009,999 | 4/1991 | Bopp . |
| 5,079,166 | 1/1992 | Winter et al. . |
| 5,100,800 | 3/1992 | Kulpa et al. . |
| 5,264,018 | 11/1993 | Koenigsberg et al. ...................... 71/63 |
| 5,342,525 | 8/1994 | Rowsell . |
| 5,389,248 | 2/1995 | Pare et al. . |
| 5,441,887 | 8/1995 | Hanson et al. ......................... 435/262.5 |
| 5,585,272 | 12/1996 | Pierce et al. .......................... 435/262.5 |

FOREIGN PATENT DOCUMENTS

| | | |
|---|---|---|
| 0 047 719 | 3/1982 | European Pat. Off. . |
| 0 167 006 | 1/1986 | European Pat. Off. . |
| 0 278 296 A2 | 1/1988 | European Pat. Off. . |
| 0 310 005 | 4/1989 | European Pat. Off. . |
| 0 589 818 | 3/1994 | European Pat. Off. . |
| 0 622 428 | 11/1994 | European Pat. Off. . |
| 244970 | 4/1987 | Germany . |
| 59 -115 789 | 7/1984 | Japan . |
| 6 -277 045 | 10/1994 | Japan . |
| 8904029 | 10/1989 | Rep. of Korea . |
| 785359 | 12/1980 | U.S.S.R. . |
| 1375394 | 11/1974 | United Kingdom . |
| 2222176 | 2/1990 | United Kingdom . |
| WO 93/06953 | 4/1993 | WIPO . |

OTHER PUBLICATIONS

Arcangeli and Arvin, 1992, "Toluene biodegradation and biofilm growth in an aerobic fixed–film reactor", Appl Microbiol Biotechnol 37:510–517.

Atkinson and Mavituna, 1991, "Immoilized microorganisms", in *Biochemical Engineering and Biotechnology Handbook*, Second Edition Stockton Press, NY p. 65.

Boronin et al., 1993, "Growth and plasmid–encoded naphthalene catabolism of *Pseudomonas putida* in batch culture", FEMS Microbiol Letters 113: 303–308.

Bossert and Young, 1986, "Anaerobic oxidation of p–cresol by a denitrifying bacterium", Appl Environ Microbiol 52(5):1117–1122.

Bouwer and McCarthy, 1983, "Transformation of halogented organic compounds under denitrification conitions", Appl Environ Microbiol 45(4):1295–1299.

Brown et al., 1993, "Critical review and case studies on biotechnology for pollution prevention", U.S. EPA, draft report.

Diekmann et al., 1990, "Effects of suboptimal environmental conditions on immobilized bacteria growing in continuous culture", Bioprocess Engineering 5:13–17.

Fries et al., 1994, "Isolation, characterization, and distribution of denitrifying toluene degraders from a variety of habitats", Appl Environ Microbiol 60(8):2802–2810.

Funk et al., 1993, "Initial–phase optimization for bioremediation of munition compound–contaminated soils", Appl Environ Microbiol 59(7):2171–2177.

Grioll et al., 1994, "Evidence for a novel pathway in the degradation of flourene by Pseudomonas sp. Strain F274", Appl Environ Microbiol 60(7):2438–2449.

Hack et al., 1994, "The production of *Pseudomonas putida* for the hydroxylation of toluene to its cis–glycol", Appl Microbiol Biotechnol 41:495–499.

Haigler et al., 1991, "Biotransformation of nitrobenzene by bacteria containing toluene degradative pathways", Appl Environ Microbiol 57:3156–3162.

Haigler et al., 1994, "Biodegradation of 2–nitrotoluene by Pseudomonas sp. Strain JS42", Appl Environ Microbiol 60(9):3466–3469.

Heitkamp et al., 1987, "Naphthalene biodegradation in environmental microcosms: Estimates of degradation rates and characterization of metabolites", Appl Environ Microbiol 53(1):129–136.

Hollender et al., 1994, "Regulation of chloro– and methylphenol degradation in *Comamonas testosteroni* JH5", Appl Environ Microbiol 60(7):2330–2338.

(List continued on next page.)

*Primary Examiner*—Ralph Gitomer
*Attorney, Agent, or Firm*—Pennie & Edmonds LLP

[57] ABSTRACT

The present invention relates to the aerobic reaction of compounds such as aromatic, nitro-aromatic, halo-aromatic, halo-nitro-aromatic, aliphatic and halo-aliphatic compounds with a microorganism, said microorganism being a member of the group consisting of microorganisms having ATCC Accession No. 55644, 55648, 55645, 55641, 55647, 55642, 55643, 55646, 55649, 55722, 55723, 55726, 55727, 55724, and 55725. More particularly, the present invention relates to the aerobic degradation of organic compounds in fluid or solid phase such that the compounds are bioremediated to products

21 Claims, 7 Drawing Sheets

OTHER PUBLICATIONS

Jung et al., 1995, "Biodegradation of nitrobenzene through a hybrid pathway in *Pseudomonas putida*", Biotechnol Bioeng 48:625–630.

Klecka and Maier, 1988, "Kinetics of microbial growth on mixtures of pentachlorophenol and chlorinated aromatic compounds", Biotechnology and Bioengineering 31:328–335.

Landa et al., 1994, "Cometabolic degradation of trichloroethylene by *Pseudomonas cepacia* G4 in a chemostat with toluene as the primary substrate", Appl Environ Microbiol 60(9):3368–3374.

Mihelcic and Luthy, 1988, "Microbial degradation of acenaphthene and naphthalene under denitrification conditions in soil–water systems", Appl Environ Microbiol 54(5):1188–1198.

Nishino et al., 1993, "Degradation of nitrobenzene by a *Pseudomonas pseudoalcaligenes*", Appl Environ Microiol 59:2520–2525.

Oltmanns et al., 1988, "Degradation of 1,4–dichlorobenzene by enriched and constructed bacteria", Appl Microbiol Biotechnol 28:609–616.

Ortega–Calvo and Alexander, 1994, "Roles of bacteria attachment and spontaneous partitioning in the biodegradation of naphthalene initially present in nonaqueous–phase liquids", Appl Environ Microbiol 60(7):2643–2646.

Pettigrew et al., 1991, "Simultaneous biodegradation of chlorobenzene and toluene by a Pseudomonas strain", Appl Environ Microbiol 57(1):57–162.

Pierce et al., 1984, "Cloning of the chlorotoluene gene", Dev ind Microbiol 25:597–602.

Pierce et al., 1983, "Immobilization of kluyvera sp.: Effect of support material upon fermentation"Dec Ind Microbiol 24:499–507.

Romanov et al., 1993, "Oxidative dehalogenation fof 2–chloro– and 2,4 dichlorobenzoates by *Pseudomonas aeruginosa*", Microbiology 62(5):532–536.

Schowanek and Verstraete, 1990, "Phosphonate utilization by bacterial cultures and enrichments from environmental samples", Appl Environ Microbiol 56(4):895–903.

Spain and Gibson, 1988, "Oxidation of substituted phenols by *Pseudomonas putida* F1 and Pseudomonas sp. strain JS6", Appl Environ Microbiol 54(6):1399–1404.

Speitel et al., 1989, "Biodegradation of trace concentrations of substituted phenols in granular activated carbon columns", Environ Sci Technol 23(1):68–74.

Stanier et al., 1966, "The aerobic pseudomonada: A taxonomic study", J. Gen Micro biol 43:159–271.

Taeger et al., 1988, "Biodegradability of mixtures of chloro– and methylsubstituted aromatics: Simultaneous degradation of 3–chlorobenzoate and 3–methylbenzoate", Appl Microbiol Biotechnol 28:603–608.

Taylor and Amador, 1988, "Metabolism of pyridine compounds by phthalate–degrading bacteria", Appl Environ Microbiol 54(10):2342–2344.

Valo and Salkinoja–Salonen, 1986, Bioreclamation of chlorophenol–contaminated soil by composting, Appl Microbiol Technol 25:68–75.

Venkataramani and Ahlert, 1984, "Rapid aerobic biostabilization of high–strength industrial land fill leachate", Journal WPCF 56(11):1178–1184.

Villiesid and Lilly, 1992, "Influence of dissolved oxygen tension on the synthesis of catechol 1,2–dioxygenase by *Pseudomonas putida*" Enzyme Microb Technol 14:561–565.

Wackett et al., 1987, "Bacterial carbon–phosphorous lyase: Products, rates, and regulation of phosphonic and phosphinic acid metabolism"J Bacteriol 169(2):710–717.

Westmeier and Rehm, 1985, "Biodegradation of 4–chlorophenol by entrapped Alcaligenes sp. A 7–2", Appl Microbiol Biotech 22:301–305.

SYSTEMS AND METHODS FOR BIODEGRADATION

The present invention is a continuation-in-part of the following co-pending applications: application Ser. No. 08/357,822, now U.S. Pat. No. 5,688,685; application Ser. No. 08/357,686; now U.S. Pat. No. 5,633,164; application Ser. No. 08/357,700, now U.S. Pat. No. 5,585,272; and application Ser. No. 08/357,821, now U.S. Pat. No. 5,571,705, which were all filed on Dec. 16, 1994.

FIELD OF THE INVENTION

This invention is related to the aerobic degradation of compounds such as aromatic, nitro-aromatic, halo-aromatic, halo-nitro-aromatic, aliphatic and halo-aliphatic compounds. These compounds are aerobically degraded by novel microorganisms to products comprising $CO_2$ and $H_2O$ using a variety of methods. The microorganisms are also capable of aerobically bioremediating compositions containing these compounds. Further, the microorganisms described herein are capable of aerobically bioremediating nitro- and halo-substituted aromatic compounds to products comprising $CO_2$ and $H_2O$ without the production of toxic intermediates or by-products.

This invention is further related to fluid phase systems and methods for aerobic reaction of compounds such as aromatic, nitro-aromatic, halo-aromatic, halo-nitro-aromatic, aliphatic and halo-aliphatic compounds. In particular embodiments, elastomeric solids or sludges containing such compounds are converted to fluidized compositions suitable for aerobic reaction. In certain embodiments, the fluidized compositions comprise slurries for aerobic bioremediation of waste materials containing organic compounds or mixtures thereof.

This invention is further related to solid phase systems and methods for aerobic degradation of compounds such as aromatic, nitro-aromatic, halo-aromatic, halo-nitro-aromatic, aliphatic and halo-aliphatic compounds in solids, sludges or soils.

This invention additionally relates to a two step process for bioremediation of waste materials containing at least one compound selected from heavily halogenated organic compounds, for example, polychlorinated biphenyls, polybrominated biphenyls, etc., heavily nitrated compounds, such as trinitrotoluene, etc., and heavily nitrated and cross-linked polymeric compounds, e,g., nitrocellulose, etc. According to this embodiment, the waste material is first combined with a reagent capable of at least partially degrading said compounds in the waste material and then contacted with the novel microorganisms which aerobically degrade any aromatic, substituted aromatic or aliphatic compounds present in the treated waste material.

This invention further relates to systems for bioremediation of gases, aerosols, and fluids including liquids using the novel microorganisms immobilized on a solid support.

BACKGROUND OF THE INVENTION

The use of microorganisms to treat waste or waste contaminated material is well documented. At the February, 1990, symposium which preceded the "EPA-Industry Meeting on Environmental Applications of Biotechnology" the EPA noted that biotechnology has been successfully utilized to treat soils and sludges from superfund sites which include contaminants from multiple and varied sources. Economic and environmental considerations indicate that bioprocessing technologies offer a significant potential for the remediation and treatment of waste and waste contaminated materials. The use of ultimate disposal technologies such as incineration or chemical fixation and encapsulation results in very large expenditures of capital, in addition to the liability associated with the handling and transport of these materials to the disposal site. Biodegradation methods entail a lower cost relative to most other approaches because they are conducted on site and use less complicated equipment. Furthermore, they can be conducted using a combination of above-ground and in situ treatments for a total treatment approach.

Examples of microbial degradation or treatment of compounds are well known in the art. For instance, U.S. Pat. Nos. 4,843,007 and 4,876,201 disclose the aerobic treatment of polychlorinated biphenyls (PCBs) and acetophenones with *Alcaligenes*, however, there is no disclosure of aromatic ring cleavage, indicating that the compounds were not degraded to the point of mineralization. Further, U.S. Pat. Nos. 5,009,999 and 4,876,201 disclose aerobic treatment of PCBs with *Pseudomonas* as well, also with no evidence of ring cleavage. U.S. Pat. No. 4,493,895 discloses the aerobic treatment of halogenated organic compounds with *Pseudomonas cepacia*, whereas U.S. Pat. No. 5,100,800 discloses treatment of the same compounds with *Pseudomonas putida* strain UNK-1.

Halo-aliphatic compounds, such as trichloroethylene or dimethylammonium chloride have also been shown to be aerobically degraded. Specific examples are found in U.S. Pat. Nos. 4,713,343 (trichloroethylene), 4,492,756 (dimethylammonium chloride), and 5,079,166 (trichloroethylene).

Funk et al., 1993, Appl. Environ. Microbiol. 59:7, pp. 2171–2177 describes a two-step in situ treatment process for soils contaminated with 2,4,6-trinitrotoluene, hexahydro-1,3,5-trinitro-1,3,5-triazine and octahydro-1,3,5,7-tetranitro-1,3,5,7-tetraazocine. The soil is first flooded with an aqueous buffer and starch to promote bacterial activity. The aerobic heterotrophs in the soil or added as inoculum quickly remove the oxygen from the soil creating anaerobic conditions. Under anaerobiosis the contaminating compounds were partially degraded by the microorganisms. They were, however, not degraded to $CO_2$ and $H_2O$, because only the substituted nitro groups were reduced and the aromatic ring was not cleaved.

Venkataramani and Ahlert, 1984, J. WPCF, 56:11, pp. 1178–1184, disclose the use of acclimated bacteria from a sewage treatment plant to aerobically degrade contaminants in an industrial landfill leachate.

The bulk of the published literature, on biodegradation, is focused on the degradation of single pure chemical by pure cultures and not on the degradation of complex mixtures of organic pollutants by mixed cultures or microbial consortia. Much of the work with pure chemicals also has been conducted at concentrations which are orders of magnitude lower than those commonly encountered with industrial wastes. For example Speitel et al., 1989, Environ. Sci. Technol. 23:68–74) examined the degradation of phenols (e.g. p-nitrophenol, 2,4-dinitrophenol, and pentachlorophenol) using pure chemicals at very low levels, i.e., 1–100 ppb. Similarly, Arcangeli and Arvin, 1992, Appl. Microbiol. Biotechnol. 37:510–517, employed very low toluene concentrations, less than 1 ppm to 6 ppm, in their bioreactor.

In controlled microcosm studies, Heitkamp, et al., 1987, Appl. Environ. Microbiol. 53:129–136), showed that naphthalene, when added to selected soil microcosms at levels of less than 1 ppm could be effectively mineralized within 17 to 31 days.

The degradation of methyl-substituted aromatics, in nature, is generally regarded to occur via the meta-cleavage pathway. However, the degradation of halo-organics, such as, for example, chlorobenzoate, proceeds best through the ortho-cleavage pathway. Knackmuss, (Taeger, et al., 1988, Appl. Microbiol. Biotechnol. 28:603–608; Romanov, et al., 1993, Microbiology 62:887–896) and Pierce (Pierce, et al. 1983, Dev. Ind. Microbiol. 24:499–507; Pierce, et al., 1984, Dev. Ind. Microbiol. 25:597–602), have shown that microorganisms can be enriched which are capable of degrading both methyl- and chloro-aromatics via the ortho-pathway. Likewise, Oltmanns, et al., 1988, Appl. Microbiol. Biotechnol. 28:609–616) have shown that bacteria enriched from nature can be constructed which are capable of degrading 1,4-dichlorobenzene via a modified ortho-pathway, not present in the wild-type strains.

Boronin and coworkers (Boronin et al., 1993, FEMS Microbiol. Letters. 113:303–308) in preparing various naphthalene plasmid constructs in *P. putida* have shown that when naphthalene is the sole carbon and energy source, the highest specific growth rates are observed with meta-pathway>ortho-pathway>gentisate-pathway.

The degradation of mixed organic substrates, and mixed, substituted aromatics in particular, increases considerably the biochemical complexity of degradation, and the regulatory and physiological control of these degradative processes. A key factor in the degradation of mixed organic substrates, particularly where pathways are inducible, is how the cultures are originally grown (and thus, induced).

Hollander, et al., 1994, Appl. Environ. Microbiol. 60:2330–2338) have noted that *Commamonas testosteroni* (previously classified as *Pseudomonas testosteroni*) degrades 4-chlorophenol and 4-methylphenol sequentially and not simultaneously. This degradation occurs via the meta-pathway.

However, where multiple organic compounds were supplied, which were degraded only via the meta-pathway, degradation was simultaneous. Because of the prior induction of the meta-pathway, degradation of compounds which proceed via the ortho-pathway required additional treatment time, because the proper enzymes had to be induced to achieve adequate levels of degradation of these compounds. In such cases, this requirement for increased treatment time has a direct negative impact on treatment economics.

Recently, Grifoll et al., 1994, Appl. Environ. Microbiol. 60:2438–2449) have isolated a *Pseudomonas* sp. (strain F274) which is capable of metabolizing fluorene, and when grown in the presence of p-hydroxybenzoate, cleaves p-hydroxybenzoate via the ortho-pathway. This strain, however, is incapable of utilizing toluene, naphthalene or benzene.

The same situation was observed by Pettigrew et al., 1991, Appl. Environ. Microbiol. 57:157–162) with the degradation of chlorobenzene and toluene by a *Pseudomonas* strain, that until the meta-pathway was repressed/modified, the simultaneous degradation of organics metabolized via the meta-pathway and ortho-pathway was not possible.

Viliesid and Lilly, 1992, Enz. Microb. Technol. 14:561–565 have shown that the basal or induced levels of catechol 1,2-dioxygenase (the key enzyme of the ortho-pathway) are directly influenced by the dissolved oxygen tension. Based upon their observations it was necessary for the oxygen tension to be above 4% of saturation (at the initiation of degradation) in order to maintain active ortho-pathway degradation.

In the recent literature, there are examples of cases where higher concentrations (1000 ppm) of phenol, Brown et al., 1993, Critical Review and Case Study on Biotechnology for Pollution Prevention, United States EPA; Hinteragger, et al. 1992 or xylene, Wolfram et al., 1990, NTIS Report No. EGG-M-90407, p.17, in aqueous solutions have been successfully degraded.

However, care should be taken to discriminate between primary metabolism and co-metabolism or resting cell metabolism. See, for example, Spain and Gibson (1988, Appl. Environ. Microbiol. 54:1399–1404), which shows resting cell metabolism of nitrophenols by toluene grown cells; and Taylor and Amador, (1988, Appl. Environ. Microbiol. 54:2342–2344) which shows resting cell metabolism of pyridine by phthalate grown cells.

By definition, heterotrophic bacteria utilize various forms of organic carbon as a source of carbon and energy. In addition to a carbon source, heterotrophic bacteria also require nitrogen and phosphorous for growth. Most commonly, inorganic forms of nitrogen or phosphorous are supplied to meet this requirement, though the use of organic nitrogen in the form of amino acids (amino nitrogen) also have been used historically. While documented in the literature, meeting nitrogen requirements through the use of hydrocarbons which contain nitrogen, e.g., heterocycles or nitrophenol or the use of organic phosphorous compounds e.g., phosphinates is less practiced, Wackett, et al., 1987, J. Bacteriol 169:710–717; Schowanek and Verstraete, 1990, Appl. Environ. Microbiol. 56:895–903. Glyphosate degradation in nature is accomplished by bacteria which not only utilize the organic carbon of this pesticide for growth and energy but utilize the organic phosphorous of glyphosate as the source of phosphorous. In fact, glyphosate degradation in nature is suppressed if other more available forms of inorganic phosphorous are present.

While there is considerable interest in using co-metabolic activity to degrade selected organic wastes, such as TCE, the use of co-metabolic processes to treat mixed wastes is likely to be inefficient, and therefore, ultimately more costly. Klecka and Maier, 1988, Biotechnol. Bioeng. 31:328–335) have shown that when degradable but non-utilizable carbon sources are added to a mixed population of pentachlorophenol degrading bacteria, the rate of pentachlorophenol degradation decreases. When however, utilizable forms of hydrocarbons are added to the mixture, the overall removal rate increases. This increase is due to an increase in biomass which results in overall improvement in degradation.

The aerobic degradation of selected aromatics and polyaromatic hydrocarbons (PAHS) is well documented. However, the aerobic degradation of compounds where present in elastomeric or tarry compositions has never been reported to the knowledge of the present inventor(s). Under conditions of anaerobic respiration (i.e. nitrate reduction/ denitrification) the oxidative degradation of these same selected chemicals has been reported, using nitrate as the terminal electron acceptor, Bossert and Young, 1986, Appl. Environ. Microbiol. 52:1117–1122; Bouwer and McCarty, 1983, Appl. Environ. Microbiol., 45:1295–1299. However, the degradation of compounds such as naphthalene is not rapid under nitrate respiration. Mihelcic and Luthy, 1988, Appl. Environ. Microbiol. 54:1188–1198 demonstrated that approximately 63 days were required to degrade naphthalene at a concentration of 1 ppm under denitrifying conditions.

Fries et al., 1994, Appl. Environ. Microbiol., 60:2802–2810, generally indicates that biodegradation of benzene, toluene, ethylbenzene and xylenes under aerobic conditions is well known, although the availability of oxygen due to its low solubility in water and low rate of transport in soils and sediments often becomes rate limiting. Fries describes anaerobic respiration of toluene by microorganisms isolated from nature using ≦0.5 ppm toluene. The microorganisms could grow on 25 ppm toluene and could be fed 50 ppm toluene. There has been no demonstration that these microorganisms can degrade any higher concentrations of toluene.

Ortega-Calvo and Alexander, 1994, Appl. Environ. Microbiol. 60:2643–2646, have speculated that two physiologically different populations, one free-swimming and the other at the organic interface are involved in the degradation of compounds such as naphthalene (when supplied at concentrations of 0.1–1.0 ppm). From their observations, it appears that the initial activity is conducted by the free-swimming bacteria, which are dependent upon the partitioning of naphthalene to the aqueous phase.

Recently, Hack, et al., 1994, Appl. Microbiol. Biotechnol. 41:495–499 have shown that cells of *P. putida* when grown on glucose, lost over 50% of this activity within 90 hours when stored at 4° C.

Considerable interest has been raised lately regarding the co-metabolism of trichloroethylene, TCE, by the recombinant strain *P. cepacia* G4 when grown on toluene. From the recent paper by Landa et al., 1994, Appl. Environ. Microbiol., 60:3368–3374, several conclusions can be drawn. It takes considerable amounts of toluene to degrade a small amount of TCE. Approximately 64 ppm of toluene is required to metabolize 3.2 ppm of TCE (a ratio of 20 parts toluene degraded for each part of TCE degraded). Furthermore, when the TCE concentration exceeds 19 ppm, competitive inhibition of toluene degradation results in the loss of TCE co-metabolism and the cessation of toluene degradation.

Immobilized and entrapped bacterial processes have been established for many years (Atkinson and Movituna, 1991, Biochemical Engineering and Biotechnology Handbook: 2nd Ed. Stockton Press, N.Y.). These processes claim to provide additional benefit with respect to improving the ruggedness of the microorganisms. For example, Dickman, et al., 1990, Bioprocess Eng'r 5:13–17, showed improved stability to oxygen deprivation and pH shocking in an immobilized continuous culture reactor versus free swimming bacteria. Westmeier and Rehm, 1985, Appl. Microbiol. Biotechnol. 22:301–305 have shown that immobilized cells of *Alcaligenes* sp. degrade 4-chlorophenol at faster rates than do free-swimming cells when fed 4-chlorophenol at low concentrations (i.e., ≦19 ppm).

Haigler, et al., 1994, Appl. Environ. Microbiol., 60:3466–3469, describes the isolation of a strain of *Pseudomonas* (strain JS42) based upon its ability to degrade and utilize 2-nitrotoluene (2-NT) as a sole source of carbon, energy, and nitrogen. While this reference shows that this strain was able to utilize 2-nitrotoluene, Haigler specifically states that *Pseudomonas* strain JS42 is incapable of utilizing nitrobenzene. In addition, Haigler makes no mention regarding the ability to degrade or utilize aniline or naphthalene. While washed cells of strain JS42 grown on 2-NT are capable of oxidizing nitrobenzene, the reference specifically makes clear that the cells cannot utilize nitrobenzene. Therefore, this biotransformation activity is more correctly defined as co-metabolism.

Composting of hazardous organic wastes represents a relatively novel application of biotreatment technology. Most notable is the example of composting of chlorophenols (Valo and Salkinoja-Salonen, 1986, Appl. Environ. Microbiol. 25:68–75). However, the time required to treat contaminated soils using this technology is not rapid (>4 months). Part of the problem with the use of composting for chlorophenols is the development of a significant level of active chlorophenol degraders. While this problem was addressed, in part, by Valo and Salkinoja-Salonen (Id., 1986), through the addition of microbial amendments, this was only possible when the soil had been previously sterilized to kill-off the indigenous microflora.

U.K. Patent No. 1,375,394 states generally that microorganisms of the genera *Pseudomonas, Mycobacterium, Flavobacterium* or *Sarcina* can aerobically degrade nitro-aromatic compounds. This reference states that the microorganisms must be induced to have the ability for such degradative activity. However, there is no indication at all regarding what concentration of nitro-aromatic should be used for induction nor any teaching of what culture conditions should be employed. Further, there is no indication in this reference at all regarding what particular species of any of the mentioned genera could be induced to have the desired degradative activity, nor is there any indication where such microorganisms could be found.

European Patent Publication No. 0278296 generally describes a method for the simultaneous chemical and biological treatment of solids and liquids containing organic waste.

Thus, there remains a real need for microorganisms and for systems and processes which are useful for rapid, efficient aerobic degradation of aromatic, nitro-aromatic, halo-aromatic, halo-nitro-aromatic, aliphatic and halo-aliphatic compounds. There is also a real need for degrading any or all of these compounds when present in elastomeric or tarry materials.

Citation or identification of any reference in Section 2 of this application shall not be construed as an admission that such reference is available as prior art to the present invention.

SUMMARY OF THE INVENTION

Novel isolated microorganisms, in pure or mixed culture, are provided which are useful for the aerobic degradation of aromatic, nitro-aromatic, halo-aromatic, halo-nitro-aromatic, aliphatic and halo-aliphatic compounds or mixtures thereof. The microorganisms are advantageously useful for the aerobic degradation of said compounds when contained in elastomeric and/or tarry solids, sludges, or soils as well as when contained in non-elastomeric compositions. The microorganisms are also useful for the degradation of such compounds or mixtures thereof in the form of gases, aerosols or fluids, including liquids. Biofilters comprising the microorganisms are provided.

The microorganisms can be stored for extended periods of time, e g., at least 4 months, without loss of degradative activities. In addition, the microorganisms can rapidly and efficiently degrade relatively high concentrations of said compounds or mixtures thereof. Further, the microorganisms can tolerate a wide range of concentrations of said compounds. The microorganisms are capable of utilizing at least one of the compounds as a sole source of carbon and energy. Certain of the microorganisms are capable of utilizing at least one of the compounds as a sole source of carbon and nitrogen.

Novel methods for fluid phase and solid systems advantageously useful for aerobic reactions of compounds are provided.

In a particularly advantageous embodiment of the fluid phase systems, novel methods for the rapid and efficient degradation of at least one compound selected from aromatic, nitro-aromatic, halo-aromatic, halo-nitro-aromatic, aliphatic and halo-aliphatic compounds or mixture thereof contained in elastomeric and/or tarry solids, sludges or soils are provided.

In a particularly advantageous embodiment of the solid phase systems, novel methods for the rapid and efficient degradation of at least one compound selected from aromatic, nitro-aromatic, halo-aromatic, halo-nitro-aromatic, aliphatic and halo-aliphatic compounds or mixture thereof contained in an elastomeric and/or tarry solid, sludge or soil are provided.

The fluid phase and solid phase systems, can be scaled up to efficiently handle a wide variety of influent feeds in time periods considerably shorter than conventional methods employed for biodegradation of aromatic and/or aliphatic compounds.

According to one embodiment of the present invention, a method for the aerobic degradation of aromatic and/or substituted aromatic compounds is provided. In general, the method entails contacting an aromatic compound with a mixed or pure culture of a microorganism, said microorganism being a member of the group consisting of microorganisms having ATCC Accession No. 55644, 55648, 55645, 55641, 55647, 55642, 55643, 55646, 55649, 55722, 55723, 55726, 55727, 55724, and 55725. In one mode of this embodiment, at least one compound selected from the group of aromatic, nitro-aromatic, halo-aromatic, halo-nitro-aromatic, aliphatic and halo-aliphatic compounds is aerobically degraded. In another mode of this embodiment, a mixture of at least two compounds selected from the group consisting of aromatic, nitro-aromatic, halo-aromatic, halo-nitro-aromatic, aliphatic and halo-aliphatic compounds is aerobically degraded. The method may further comprise culturing the microorganisms in contact with said compound(s) so that the aromatic compound or compounds are degraded to products comprising $CO_2$ and $H_2O$.

According to another embodiment of the invention, fluid phase systems and methods for aerobic reaction of compounds are provided. Most generally, the fluid phase systems entail converting an elastomeric solid or sludge into a fluidized composition suitable for aerobic reaction of organic compounds contained in the elastomeric solid or sludge. The aerobic reactions for which the fluidized compositions are useful include synthetic as well as degradative reactions which take place preferably under aerobic conditions.

The method for preparing a fluidized composition suitable for aerobic reaction comprises the steps of: (a) particularizing an elastomeric solid or sludge containing an organic compound; and (b) contacting the particularized solid or sludge in a vessel with a current of fluid selected from the group consisting of oxygen, oxygen containing gas, including air, water and an aqueous solution, such that the particularized solid or sludge is suspended or dispersed in the current of fluid to form a composition suitable for aerobic reaction of an organic compound contained in the solid or sludge.

The method can further comprise combining the elastomeric solid or sludge with a detackifying agent either simultaneously with or subsequent to step (a).

According to another embodiment of the present invention, fluid phase systems and methods for aerobic degradation of compounds using microorganisms are provided. A fluid phase which is a slurry formed from, for example, a solid, soil, and/or sludge is produced.

A fluid phase which is a slurry can be formed from either non-elastomeric or an elastomeric solid, sludge or soil. Such slurries are used to aerobically degrade an aromatic or aliphatic compound or mixture thereof contained in said solid, sludge or soil.

The method comprises (a) combining said solid or sludge with water or an aqueous solution; and (b) imparting energy to said solid or sludge/aqueous combination in a vessel such that said solid or sludge is fluidized into a slurry.

Energy can be imparted, for example, by imparting mechanical energy, e.g., by mixing; by imparting acoustic energy; e.g., by setting up a standing acoustic wave in the slurry materials; or by imparting an electrical or electrostatic field.

In one alternative embodiment, the method comprises (a) combining an elastomeric solid or sludge with water or an aqueous solution; (b) imparting energy to said elastomeric solid or sludge/water combination such that said solid or sludge is fluidized into a slurry; and (c) separating said slurry away from any residual elastomeric solid or sludge.

Alternatively, the method comprises (a) combining an elastomeric solid or sludge with a detackifying agent to form a solid or sludge/detackifying agent combination; (b) combining said solid or sludge with water or an aqueous solution to form a solid or sludge/detackifying agent aqueous combination; and (c) imparting energy to said solid or sludge/detackifying agent aqueous combination such that said detackified solid or sludge is fluidized into a slurry. This method can further comprise mixing said solid or sludge/detackifying agent combination to form a detackified solid or sludge. In still another alternative, the method comprises (a) combining an elastomeric solid or sludge with a detackifying agent and water or an aqueous solution; and (b) imparting energy to said mixture formed in step (a) such that said elastomeric solid or sludge is fluidized into a slurry.

According to the present invention, a method for slurry phase bioremediation of solids, sludges or soils containing at least one compound or a mixture of at least two compounds selected from the group consisting of aromatic, nitro-aromatic, halo-aromatic, halo-nitro-aromatic, aliphatic and halo-aliphatic compounds comprises (a) adjusting the pH of a slurry towards neutrality, if necessary; and (b) contacting said neutral slurry with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. The method can further comprise culturing said microorganisms with said slurry such that the compound is degraded to products comprising $CO_2$ and $H_2O$.

The methods for solid phase bioremediation of solids, sludges or soils containing at least one compound or a mixture of at least two compounds selected from the group consisting of aromatic, nitro-aromatic, halo-aromatic, halo-nitro-aromatic, aliphatic and halo-aliphatic compounds comprise (a) mixing said solid, sludge or soil with a bulking agent such that a fluid, for example, air, can readily pass through the bulked mixture; (b) adjusting the pH of the bulked mixture towards neutrality, if necessary; and (c) contacting said bulked mixture with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. The methods can further comprise culturing said microorganisms with said bulked solid, sludge or soil such that said compound is degraded to products comprising $CO_2$ and $H_2O$.

Where the solid, sludge or soil is a tarry or elastomeric solid, sludge or soil, the methods for solid phase bioremediation comprise: (a) mixing a tarry or elastomeric solid, a tarry or elastomeric sludge or a tarry or elastomeric soil with a detackifying agent such that said solid soil or sludge forms a particularized less tarry and/or elastomeric mixture.

Another embodiment of the present invention is a biofilter and methods for its use. Biofilters are used in the bioremediation of compounds in effluents such as air, vapors, aerosols, and water or aqueous solutions.

According to yet another embodiment of the invention, a two step method for aerobic degradation of waste materials containing at least one compound, selected from heavily halogenated organic compounds such as polychlorinated biphenyls, polybrominated biphenyls, etc., heavily nitrated compounds, such as trinitrotoluene, etc., and heavily nitrated and cross-linked polymeric compounds, e.g., nitrocellulose, etc. is provided. The waste materials can further comprise as a compound selected from the group consisting of aromatic, nitro-aromatic, halo-aromatic, halo-nitro-aromatic, aliphatic and halo-aliphatic compounds or a mixture of such compounds. The methods comprise: (a) combining a reagent capable of chemically degrading, at least partially, a heavily halogenated, a heavily nitrated or a heavily nitrated cross-linked compound in a waste material to form a pretreated composition; and (b) contacting said pretreated composition with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. The method can further comprise culturing said microorganisms such that at least one compound is degraded to products comprising $CO_2$ and $H_2O$.

The speed and efficiency afforded by the methods of the present invention have been never before achieved for the bioremediation of tarry or elastomeric compositions containing either a single or a mixture of aromatic, nitro-aromatic, halo-aromatic, halo-nitro-aromatic, aliphatic and halo-aliphatic compound(s).

The present invention may be understood more fully by reference to the following definitions, detailed description of the invention, illustrative examples of specific embodiments of the invention and the appended figures in which:

BRIEF DESCRIPTION OF THE FIGURES

FIG. 1a illustrates a slurry formation system; FIG. 1b illustrates a fluid phase bioremediation system; and FIG. 1c illustrates filtration and dewatering of treated materials.

FIG. 2. Schematic diagram for slurry phase formation.

DEFINITIONS

Figure 1A:
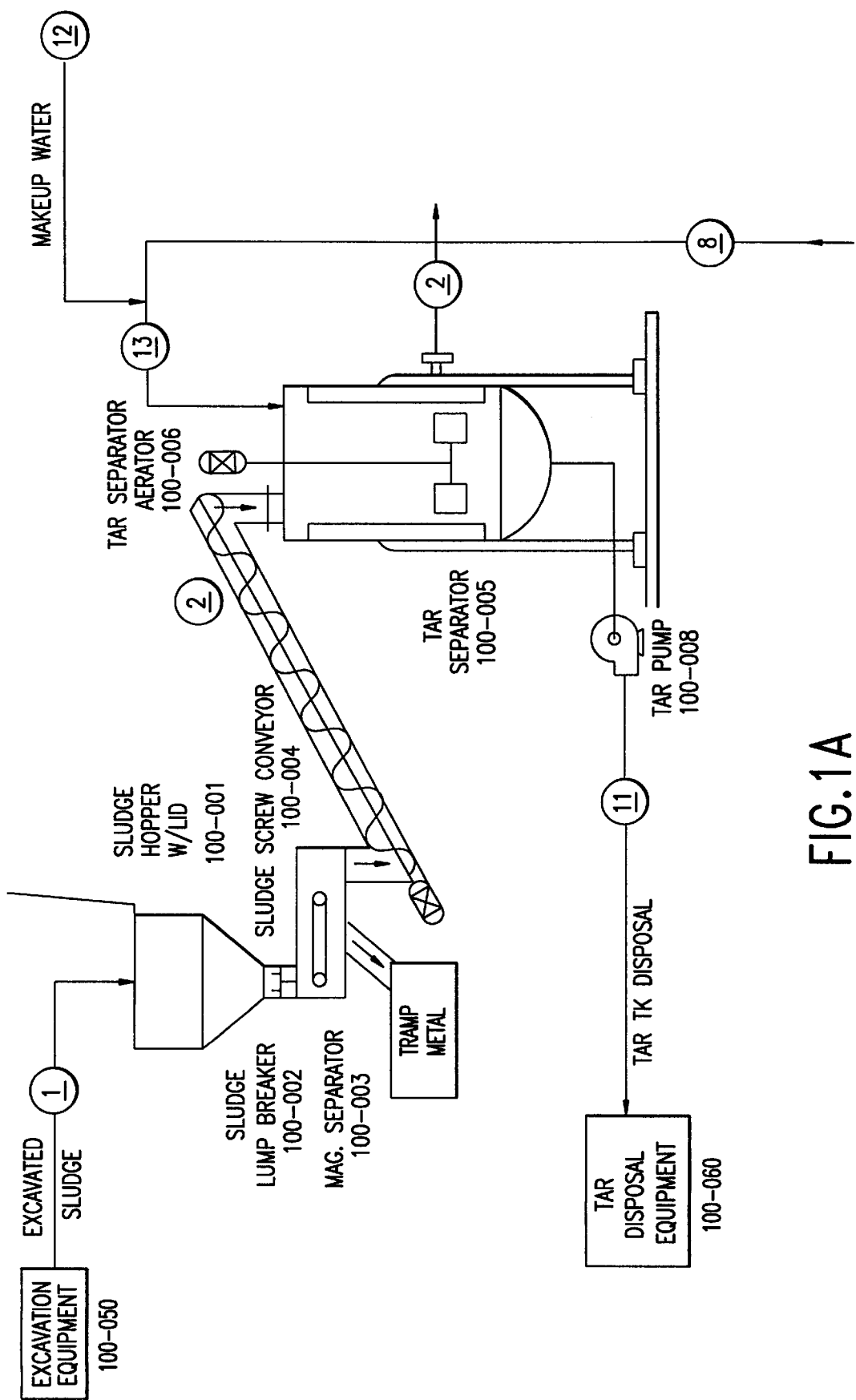
FIGS. 1a–c. A schematic illustration of a representative fluid phase system.

As used in the present invention, the following terms are intended to encompass the following:

AEROBIC Pertaining to or requiring oxygen wherein the oxygen tension is 0.1% to 100% of saturation (where, 100% saturation corresponds to 40 mg $O_2$ per liter based on oxygen in water at 25° C.), preferably between 4% and 80%, more preferably between 10% and 20%.

ALKYL A methyl, ethyl or propyl group.

ALIPHATIC An acyclic or alicyclic organic hydrocarbon compound that can be regarded as a derivative of methane and lacks a cyclic conjugated six-member carbon (benzene) ring.

AROMATIC An organic compound which is characterized by the presence of at least one cyclic fully conjugated six-member carbon (benzene) ring or one cyclic fully conjugated hetero-six-member ring in which one or more ring carbon(s) is replaced by a nitrogen atom(s). This is intended to include non-substituted aromatic compounds as well as aromatic compounds containing one or more of the following in place of a hydrogen atom(s): a hydroxyl, an amine, an alkyl, a carboxyl, or an unsubstituted or substituted aliphatic group, in which the substituted aliphatic group contains a carbonyl or carboxyl group in place of a hydrogen atom(s).

BULKING AGENT A compound or composition that when added to a solid, sludge or soil facilitates the flow of fluid through said solid, sludge or soil.

COMPOSTING-LIKE A process wherein organic hydrocarbon compounds in a solid composition are degraded by microorganisms, usually in a closed or confined area.

DETACKIFYING AGENT A compound that when mixed with an elastomeric or tarry substance renders the substance less elastomeric or tarry. When used in conjunction with the process for forming a slurry, the detackifying agent aids in the compositions becoming fluidizable.

ELASTOMERIC The property whereby a solid material changes its shape and size under the action of opposing forces, but recovers its original configuration when the forces are removed, provided the opposing forces do not exceed the elastic modulus of the solid material.

HALO-ALIPHATIC An aliphatic hydrocarbon compound containing one or more halogen atoms such as, for example, chlorine, bromine or iodine or a mixture thereof in place of an hydrogen atom(s).

HALO-AROMATIC An aromatic hydrocarbon compound containing one or more halogen atoms such as, for example, chlorine, bromine or iodine or a mixture thereof in place of a hydrogen atom(s).

HALO-NITRO-AROMATIC An aromatic hydrocarbon compound containing one or more halogen atoms such as, for example, chlorine, bromine or iodine or a mixture thereof in place of a hydrogen atom(s) and containing one or more nitro groups in place of a hydrogen atom(s).

FLUIDIZING A process wherein energy, such as, for example, mechanical energy, is imparted to suspend finely divided or particularized solids in a fluid such as, for example, air, water or an aqueous solution.

NITRO-AROMATIC An aromatic hydrocarbon compound containing one or more nitro groups in place of a hydrogen atom(s).

SLUDGE A collection of solids such as, for example, a still-bottom, that have settled out of a suspension.

SLURRY A suspension of finely divided or particularized solids in a fluid or liquid wherein energy, such as, for example, mechanical energy, may be imparted to maintain dispersion of the particularized solids.

TARRY A viscous hydrocarbon containing material, which may have the consistency and appearance of roofing tar.

TCL Target Compound List, a designated list of compounds analyzed using a solvent extraction as defined in EPA, SW-846. As used presently, the extraction solvent is methylene chloride:methanol (90:10).

TCLP Toxicity Characteristic Leaching Procedure, an aqueous extraction method as defined in EPA, SW-846, Method No. 1311.

DETAILED DESCRIPTION OF THE INVENTION

6.1 Novel Isolated Microorganisms

Novel microorganisms have been isolated from soil and selected for the ability to utilize specific compounds such as aromatic, substituted aromatic and/or aliphatic compounds as sole nitrogen and/or carbon and energy sources. The microorganisms are useful for aerobic degradation of at least one of these compounds. The selection process ensured that the biochemical activity of the microorganisms is directed towards destructive treatment of at least one of such compounds and that the microorganisms are capable of utilizing at least one of the compounds as a sole nutrient source. Although the present inventor(s) does not wish to be limited to a particular mechanism of action, it is believed that such utilization results in mineralization of the compound(s) via primary metabolism and not co-metabolism. An important element in the selection of the desired microorganisms is that the selection process is conducted under aerobic conditions such that the isolated microorganisms aerobically degrade the desired compound or mixtures thereof. Further, the microorganisms may degrade mixtures simultaneously, not sequentially.

Additionally, although the present inventor(s) do(es) not wish to be limited to a particular mechanism of action, it is believed that the majority of the degradation occurs via the ortho- or modified ortho-pathway. The ortho- or modified ortho-pathway is especially important so that highly toxic halo-acids and/or non-metabolizable intermediates are not produced as intermediates or end products during the degradation of halo-aromatic compounds or aromatic compounds substituted with one or more methyl group(s). It is noted that, for example, two of the microorganisms i.e. DAP 66 and DAP 70 do possess catechol 2,3-dioxygenase activity, indicating the ability to use meta-cleavage.

Additionally, the microorganisms are isolated such that they are able to withstand high and/or variable concentrations of the compounds. Moreover, the microorganisms can degrade a high total or composite concentration of mixed organic compounds, for example, $\geq 1\%$ (10,000 ppm). As used in the present invention, "high" concentrations of aromatic, nitro-aromatic, halo-aromatic, halo-nitro-aromatic, aliphatic and halo-aliphatic compounds are intended to encompass the following: (1) aromatic compounds: for example, benzene, toluene, xylenes, ethylbenzene: $\geq 5,000$ ppm; phenol: $\geq 6,000$ ppm, creosol, dimethylphenol: $\geq 1,000$ ppm; anthracene: $\geq 300$ ppm; styrene: $\geq 5,000$ ppm; aniline: $\geq 150$ ppm; naphthalene: $\geq 1,000$ ppm; 1- or 2-methylnaphthalene: $\geq 200$ ppm; (2) nitro-aromatic compounds: for example, nitrobenzene: $\geq 150$ ppm; (3) halo-aromatic compounds: for example, chlorobenzene, 2-chloronaphthalene: $\geq 200$ ppm.

The microorganisms of the present invention can also degrade the following compounds at concentrations of at least 1000 ppm: pyrene, acenaphthylene, fluoranthene, phenanthrene, benzo-(b)-fluoranthene, dibenzofuran, chrysene, catechol, m-toluic acid, cinnamyl acetate, vanillin, trans-cinnamaldehyde, mesitylene, salicylate, 2-, 3-, or 4-chlorotoluene, 2-, 3-, or 4-chlorobenzoate, 1,3-dichlorobenzoate, 1-chloro-3-nitrobenzene, 1-chloro-4-nitrobenzene, 1,2-, 1,3-, or 1,4-dinitrobenzene, melamine, cyanuric acid, hexadecane, and $\delta$-(-)-limonene.

Preference is given in the selection process for those microorganisms which are capable of growing/metabolizing on solid surfaces and for those microorganisms which chemotactically migrate towards solid surfaces.

In general, the microorganisms isolated do not constitutively express the metabolic proteins necessary for degradation of the desired compounds but rather have to be induced by culturing on medium containing the relevant compound or mixture thereof or on medium containing a compound which induces enzymes of the pathway specific for the degradation of the relevant compound(s). In a particular embodiment, the medium contains at least one of nitrobenzene, aniline, melamine and cyanuric acid; and at least one of naphthalene, benzene, toluene, ethylbenzene and xylene.

Additionally, all of the microorganism isolates are naturally occurring strains, i.e., none of the strains are modified recombinantly.

Pure and mixed cultures of the novel microorganisms of the present invention can be maintained using BACTO™ R2A medium (Difco, Detroit, Mich.). Use of BACTO™ R2A medium as maintenance medium entails: inoculation of BACTO™ R2A medium with a pure or mixed culture according to the present invention, and culture of the microorganisms at room temperature, i.e., about 25°–27° C. for about 48 hours. The cultures can then be covered with a material which forms a barrier to passage of air and moisture, e.g., parafilm, and stored under refrigeration, for example, at about 4° C.

Alternatively, pure and mixed cultures of the microorganisms of the present invention can be maintained by culture using Stanier's minimal medium (Stanier et al., 1966, J. Gen. Microbiol. 43:159–271) supplemented with 5–10 mM of the desired aromatic, nitro-aromatic, halo-aromatic, halo-nitro-aromatic, aliphatic or halo-aliphatic compound or mixture thereof. According to a preferred mode of this embodiment a C:N ratio of about 10:1 to 25:1 is maintained in the supplemented Stanier's medium. The cultures are maintained, with aeration, for example, using pure oxygen at 100–400 ml/min and with stirring. After about 24 hours cultured on the supplemented Stanier's, the bacterial cells are removed from the medium by centrifugation, resuspended in either Stanier's minimal medium (SMM) or phosphate buffered saline (PBS), and removed from the resuspension wash by centrifugation. The cell pellet can be stored at about 4° C.

Alternatively, mixed cultures can be maintained as follows. A mixed culture can be inoculated into a composition containing the following: (1) naphthalene, preferably between about 1000–4000 ppm; (2) one or more of: benzene, toluene, ethylbenzene and xylene at about 400–500 ppm each; (3) either or both chloronaphthalene and/or methylnaphthalene at about 200 ppm each; and (4) aniline and/or nitrobenzene at about 30–300 ppm each and treated using a fluid phase or a solid phase system as described in Section 6.3, infra. Preferably the C:N:P ratio is about 25:1:0.1 and the culture is maintained at about room temperature for the treatment cycle. At the end of the treatment, the contents of the slurry phase treatment can be filtered, for example, using Whatman 1 filter or other equivalent and the dewatered residual solid, designated "filter cake" containing induced microorganisms can be used to maintain a mixed culture suitable for use according to the present invention.

Some of the microorganisms described below are capable of utilizing nitrobenzene aerobically as a sole source of carbon, nitrogen and energy. In particular, microorganisms designated DAP 111, DAP 119, DAP 622, DAP 623, DAP 626, DAP 629, DAP 632, DAP 115, DAP 120 and the mixed culture designated DAP-2 can aerobically degrade nitrobenzene. Microorganisms designated DAP 70, DAP 73, DAP 111, DAP 119 and DAP 622 and the mixed culture DAP 2 can aerobically degrade naphthalene, methylnaphthalene, chloronaphthalene or anthracene. Microorganisms designated DAP 111, DAP 119 and DAP 622, DAP 623, DAP 626, DAP 629, DAP 632, DAP 115, DAP 120 and the mixed culture DAP 2 can aerobically degrade aniline. Additionally, some of the microorganisms described below are able to utilize a wide variety of substituted and non-substituted aromatic compounds, for example, benzene, toluene, aniline, phenol and ethylbenzene, aerobically as a sole source of carbon and/or nitrogen and energy. All of the pure cultures of microorganisms described below utilize these compounds aerobically. Although not wishing to be limited to a single mechanism of action, the present inventor(s) believes that the compounds are degraded aerobically, for the most part, via the ortho- or modified ortho-pathway. The pure and mixed cultures can degrade the compounds to products comprising $CO_2$ and $H_2O$.

Some of the microorganisms described below are also able to utilize a wide variety of substituted and non-substituted aliphatic compounds, for example, δ-(-)-limonene, formaldehyde, chloroform and methanol, aerobically. In addition, some of the microorganisms are also able to degrade longer-chain aliphatic compounds. The latter ability can be evidenced, for example, by the utilization of hexadecane as a sole carbon and energy source.

All the microorganisms described below were observed to grow better, i.e., cells more rapidly developed into larger colonies, when cultured on low density agar medium, i.e., at about 3–10 gm agar per liter of medium, preferably at about 3 gm of agar per liter of medium. The microorganisms described below can be cultured on normal density agar medium, but growth is less rapid.

The motile microorganisms described below are induced to exhibit chemotaxis by a wide variety of compounds. Chemotaxis is achieved by two modes of motility, namely, flagellar and twitching. Growth conditions allow the microorganism to exhibit either of the two modes of motility. For example, to observe flagellar motility, the microorganisms are grown under less viscous conditions, for example, in liquid medium or on agar plates wherein the percentage of agar is less than about 1%, perferrably 0.3%. To observe twitching motility, the microorganisms are grown on a solid medium, such as agar plates wherein the percentage of agar is about 1%. If the percentage of agar is too high, for example about 2%, both phenotypes of chemotaxis are not likely to be observed. Certain of the motile microorganisms, including DAP 111 and DAP 119 exhibit both modes of motility under appropriate conditions.

Each of the pure cultures, as well as the mixed culture, described below in Sections 6.1.1–6.1.5, including sub-Section 6.1.5.1, were deposited with the American Type Culture Collection (see Section 10, infra).

6.1.1 Microorganism Isolated Using Nitrobenzene

The following microorganism was isolated from soil using aerobic culture on a minimal medium containing only nitrobenzene as the sole source of carbon, nitrogen and energy.

Microorganism DAP 622

DAP 622 is a *Pseudomonas* sp. Gram negative motile rod occasionally seen in pairs, and when grown on nutrient agar the colonies appear white to creamy. Floc formation is present and motility appears flagellar when the microorganism is grown on flagella plates. This organism is able to produce yellow pigment when grown on *Pseudomonas* F Agar (Difco). In addition, this organism can utilize the following: lactate, chlorobenzene, ethylbenzene, salicylate, and succinate as a sole source of carbon and energy. DAP 622 is further characterized as shown in Table 1.

TABLE 1

| DIFFERENTIAL CHARACTERISTIC | RESULT |
| --- | --- |
| CATALASE/OXIDASE | (+)/(+) |
| CITRATE UTILIZATION | (+) |
| TRIPLE SUGAR IRON AGAR | $H_2S$ is produced |
| GROWTH AT: | |
| 15° C. | (+) |
| 25° | (+) |
| 35° | (+) |
| 41° | |
| UTILIZATION OF: | |
| GLUCOSE | (+) |
| FRUCTOSE | (+) |
| LACTOSE | (−) |
| MANNITOL | (+) |
| MANNOSE | (+) |
| 2-METHYLNAPHTHALENE | (+) |
| α-KETOGLUTARATE | (+) |
| GLYOXYLATE | (−) |
| GLUTAMATE | (+) |
| ETHANOL | (+) |
| HEXADECANE | (−) |
| $NO_3 \rightarrow NO_2$ | (+) |
| ARGININE DECARBOXYLASE | (−) |
| LYSINE DECARBOXYLASE | (−) |
| ORNITHINE DECARBOXYLASE | (−) |
| GELATIN HYDROLYSIS | (+) |
| UREASE | (+) |
| ANTIBIOTIC RESISTANCE: | |
| $HgCl_2$ | R |
| AMPICILLIN | R |
| KANAMYCIN | (−) |
| NEOMYCIN | (−) |
| TETRACYCLINE | (−) |
| SPECTINOMYCIN | (R) |
| STREPTOMYCIN | (−) |

6.1.2 Microorganisms Isolated Using Chlorobenzene

The following microorganisms were isolated from soil using aerobic culture on minimal medium containing only chlorobenzene as the sole source of carbon and energy.

Microorganism DAP 631

DAP 631 is a *Pseudomonas* sp. Gram negative slender motile rod seen occasionally in pairs, colonies of the microorganism appear white on BACTO™ R2A medium. In addition, this organism can utilize the following: lactate, chlorobenzene, and ethylbenzene as a sole source of carbon and energy. DAP 631 is further characterized as shown in Table 2.

TABLE 2

| DIFFERENTIAL CHARACTERISTIC | RESULT |
|---|---|
| CATALASE/OXIDASE | (- to weak)/(+) |
| CITRATE UTILIZATION | (-) |
| TRIPLE SUGAR IRON AGAR | $H_2S$ is produced |
| GROWTH AT: | |
| 15° | (+) |
| 25° | (+) |
| 35° | (+) |
| 41° | (-) |
| UTILIZATION OF: | |
| GLUCOSE | (+) |
| FRUCTOSE | (-) |
| LACTOSE | (-) |
| MANNITOL | (-) |
| MANNOSE | (-) |
| 2-METHYLNAPHTHALENE | (-) |
| α-KETOGLUTARATE | (-) |
| GLYOXYLATE | (-) |
| GLUTAMATE | (+) |
| ETHANOL | (-) |
| HEXADECANE | (-) |
| $NO_3 \to NO_2$ | (+) |
| ARGININE DECARBOXYLASE | (-) |
| LYSINE DECARBOXYLASE | (-) |
| ORNITHINE DECARBOXYLASE | (-) |
| GELATIN HYDROLYSIS | (-) |
| UREASE | (-) |
| ANTIBIOTIC RESISTANCE: | |
| $HgCl_2$ | (-) |
| AMPICILLIN | R |
| KANAMYCIN | (-) |
| NEOMYCIN | (-) |
| TETRACYCLINE | (-) |
| SPECTINOMYCIN | (-) |
| STREPTOMYCIN | (-) |

Microorganism DAP 68

DAP 68 is a *Aeromonas* sp. Gram negative motile rod found occasionally in pairs and appears white to creamy on BACTO™ R2A medium. In addition, this organism can utilize the following: lactate, chlorobenzene, ethylbenzene, and succinate as a sole source of carbon and energy. DAP 68 is further characterized as shown in Table 3.

TABLE 3

| DIFFERENTIAL CHARACTERISTIC | RESULT |
|---|---|
| CATALASE/OXIDASE | (+)/(-) |
| CITRATE UTILIZATION | (+) |
| TRIPLE SUGAR IRON AGAR | $H_2S$ is produced acid and gas from glucose |
| GROWTH AT: | |
| 15° | (+) |
| 25° | (+) |
| 35° | (+) |
| 41° | (+) |
| UTILIZATION OF: | |
| GLUCOSE | (+) |
| FRUCTOSE | (+) |
| LACTOSE | (+) |
| MANNITOL | (+) |
| MANNOSE | (+) |
| 2-METHYLNAPHTHALENE | (-) |
| α-KETOGLUTARATE | (+) |
| GLYOXYLATE | (+) |
| GLUTAMATE | (+) |
| ETHANOL | (-) |

TABLE 3-continued

| DIFFERENTIAL CHARACTERISTIC | RESULT |
|---|---|
| HEXADECANE | (-) |
| $NO_3 \to NO_2$ | (+) |
| ARGININE DECARBOXYLASE | (+) |
| LYSINE DECARBOXYLASE | (+) |
| ORNITHINE DECARBOXYLASE | (+) |
| GELATIN HYDROLYSIS | (+) |
| UREASE | (+) |
| ANTIBIOTIC RESISTANCE: | |
| $HgCl_2$ | R |
| AMPICILLIN | R |
| KANAMYCIN | R |
| NEOMYCIN | R |
| TETRACYCLINE | R |
| SPECTINOMYCIN | R |
| STREPTOMYCIN | R |

Microorganism DAP 66

DAP 66 is a *Corynebacterium* sp. Gram variable, large, non-motile rod seen singly and in chains. Some chains approach filaments in size and some single rods are motile. Floc formation is present and the cells have capsules. Growth on twitching plates is equivocal. Colonies appear hard and waxy when grown on BACTO™ R2A medium. This organism tested positive for the first enzyme in the meta-pathway, catechol-2,3-dioxygenase (C230), according to the procedure outlined by Bayly and Wigmore, 1973, J. Bacteriol. 113:1112–1120. In addition, this organism can utilize the following: lactate, chlorobenzene, m-toluic acid, ethylbenzene, and succinate as a sole source of carbon and energy. DAP 66 is further characterized as shown in Table 4.

TABLE 4

| DIFFERENTIAL CHARACTERISTIC | RESULT |
|---|---|
| CATALASE/OXIDASE | (+)/(+) |
| CITRATE UTILIZATION | (-) |
| TRIPLE SUGAR IRON AGAR | no fermentation |
| GROWTH AT: | |
| 15° | (-) |
| 25° | (+) |
| 35° | (+) |
| 41° | (-) |
| UTILIZATION OF: | |
| GLUCOSE | (+) |
| FRUCTOSE | (+) |
| LACTOSE | (-) |
| MANNITOL | (+) |
| MANNOSE | (-) |
| 2-METHYLNAPHTHALENE | (-) |
| α-KETOGLUTARATE | (-) |
| GLYOXYLATE | (-) |
| GLUTAMATE | (-) |
| ETHANOL | (+) |
| HEXADECANE | (+) |
| $NO_3 \to NO_2$ | (-) |
| ARGININE DECARBOXYLASE | (-) |
| LYSINE DECARBOXYLASE | (-) |
| ORNITHINE DECARBOXYLASE | (-) |
| GELATIN HYDROLYSIS | (-) |
| UREASE | (+) |
| ANTIBIOTIC RESISTANCE: | |
| $HgCl_2$ | R |
| AMPICILLIN | R |
| KANAMYCIN | R |
| NEOMYCIN | (-) |
| TETRACYCLINE | (-) |

TABLE 4-continued

| DIFFERENTIAL CHARACTERISTIC | RESULT |
|---|---|
| SPECTINOMYCIN | (−) |
| STREPTOMYCIN | (−) |

6.1.3 Microorganisms Isolated Using Naphthalene

The following microorganisms were isolated from soil using aerobic culture on minimal medium containing only naphthalene as the sole source of carbon and energy.

Microorganism DAP 70

DAP 70 is a *Pseudomonas* sp. Gram negative motile rod where the rods are seen singly, in pairs or in long chains, wherein some chains approach the size of filaments. When grown on flagella plates the motility appears flagellar and when grown on BACTO™ R2A medium the colonies appear white. In addition, the microorganism forms large flocs. This organism tested positive for the first enzyme in the meta-pathway, catechol-2,3-dioxygenase (C230), according to the procedure outlined by Bayly and Wigmore, 1973, J. Bacteriol. 113:1112–1120. In addition, this organism can utilize the following: lactate, chlorobenzene, ethylbenzene, and succinate as a sole source of carbon and energy. DAP 70 is further characterized as shown in Table 5.

TABLE 5

| DIFFERENTIAL CHARACTERISTIC | RESULT |
|---|---|
| CATALASE/OXIDASE | (+)/(+) |
| CITRATE UTILIZATION | (+) |
| TRIPLE SUGAR IRON AGAR | acid from glucose |
| GROWTH AT: | |
| 15° | (+) |
| 25° | (+) |
| 35° | (+) |
| 41° | (−) |
| UTILIZATION OF: | |
| GLUCOSE | (+) |
| FRUCTOSE | (+) |
| LACTOSE | (+) |
| MANNITOL | (+) |
| MANNOSE | (−) |
| 2-METHYLNAPHTHALENE | (−) |
| α-KETOGLUTARATE | (−) |
| GLYOXYLATE | (+) |
| GLUTAMATE | (−) |
| ETHANOL | (+) |
| HEXADECANE | (+) |
| $NO_3 \rightarrow NO_2$ | (−) |
| ARGININE DECARBOXYLASE | (−) |
| LYSINE DECARBOXYLASE | (−) |
| ORNITHINE DECARBOXYLASE | (−) |
| GELATIN HYDROLYSIS | (−) |
| UREASE | (+) |
| ANTIBIOTIC RESISTANCE: | |
| $HgCl_2$ | R |
| AMPICILLIN | R |
| KANAMYCIN | R |
| NEOMYCIN | R |
| TETRACYCLINE | R |
| SPECTINOMYCIN | R |
| STREPTOMYCIN | R |

Microorganism DAP 73

DAP 73 is a *Zoogloea* sp. Gram variable motile rod found singly and in pairs. Growth on motility plates indicates mobility. Floc formation is present with many finger-like projections. This organism is able to produce yellow pigment when grown on *Pseudomonas* F Agar (Difco). In addition, this organism can utilize the following: lactate, chlorobenzene, and succinate as a sole source of carbon and energy. DAP 73 is further characterized as shown in Table 6.

TABLE 6

| DIFFERENTIAL CHARACTERISTIC | RESULT |
|---|---|
| CATALASE/OXIDASE | (+)/(+) |
| CITRATE UTILIZATION | (+) |
| TRIPLE SUGAR IRON AGAR | $H_2S$ is produced |
| GROWTH AT: | |
| 15° | (+) |
| 25° | (+) |
| 35° | (+) |
| 41° | (+) |
| UTILIZATION OF: | |
| GLUCOSE | (+) |
| FRUCTOSE | (+) |
| LACTOSE | (−) |
| MANNITOL | (+) |
| MANNOSE | (+) |
| 2-METHYLNAPHTHALENE | (+) |
| α-KETOGLUTARATE | (+) |
| GLYOXYLATE | (−) |
| GLUTAMATE | (+) |
| ETHANOL | (+) |
| HEXADECANE | (−) |
| $NO_3 \rightarrow NO_2$ | (+) |
| ARGININE DECARBOXYLASE | (−) |
| LYSINE DECARBOXYLASE | (−) |
| ORNITHINE DECARBOXYLASE | (−) |
| GELATIN HYDROLYSIS | (+) |
| UREASE | (+) |
| ANTIBIOTIC RESISTANCE: | |
| $HgCl_2$ | R |
| AMPICILLIN | R |
| KANAMYCIN | (−) |
| NEOMYCIN | (−) |
| TETRACYCLINE | (−) |
| SPECTINOMYCIN | R |
| STREPTOMYCIN | (−) |

6.1.4 Microorganisms Isolated Using Nitrobenzene and Naphthalene

The following microorganisms were isolated initially from soil and aerobically cultured to pure microorganism isolates. These pure microorganism isolates were subsequently cultured aerobically together with a sludge/waste material containing a mixture of compounds for example, naphthalene, preferably between about 1000–4000 ppm; benzene, toluene, ethylbenzene and xylene at about 400–500 ppm each; chloronaphthalene and methylnaphthalene at about 200 ppm each; and aniline and nitrobenzene at about 30–300 ppm each. In addition, substituted and non-substituted aliphatic compounds were also present in the mixture. Pure microorganism isolates were recovered from the cultured materials using aerobic culture on a minimal medium containing 150 ppm nitrobenzene and 150 ppm naphthalene as the sole sources of carbon, nitrogen and energy.

Microorganism DAP 111

DAP 111 is a *Pseudomonas* sp. Gram negative motile rod found both in pairs and singly. The colonies appear white on BACTO™ R2A medium and some floc formation occurs. Motility on both twitching and flagella plates is observed. In addition, this organism can utilize the following: lactate, vanillin, chlorobenzene, ethylbenzene, cyanuric acid, salicylate, and succinate as a sole source of carbon and energy. DAP 111 is further characterized as shown in Table 7.

TABLE 7

| DIFFERENTIAL CHARACTERISTIC | RESULT |
|---|---|
| CATALASE/OXIDASE | (+)/(+) |
| CITRATE UTILIZATION | (+) |
| TRIPLE SUGAR IRON AGAR | $H_2S$ is produced |
| GROWTH AT: | |
| 15° | (+) |
| 25° | (+) |
| 35° | (+) |
| 41° | (+) |
| UTILIZATION OF: | |
| GLUCOSE | (+) |
| FRUCTOSE | (+) |
| LACTOSE | (−) |
| MANNITOL | (+) |
| MANNOSE | (+) |
| 2-METHYLNAPHTHALENE | (+) |
| α-KETOGLUTARATE | (+) |
| GLYOXYLATE | (+) |
| GLUTAMATE | (+) |
| ETHANOL | (−) |
| HEXADECANE | (+) |
| $NO_3 \rightarrow NO_2$ | (+) |
| ARGININE DECARBOXYLASE | (−) |
| LYSINE DECARBOXYLASE | (+) |
| ORNITHINE DECARBOXYLASE | (−) |
| GELATIN HYDROLYSIS | (+) |
| UREASE | (+) |
| ANTIBIOTIC RESISTANCE: | |
| $HgCl_2$ | R |
| AMPICILLIN | R |
| KANAMYCIN | R |
| NEOMYCIN | R |
| TETRACYCLINE | R |
| SPECTINOMYCIN | R |
| STREPTOMYCIN | (−) |

Microorganism DAP 119

DAP 119 is an *Aeromonas* sp. Gram negative motile rod. The colonies appear white on BACTO™ R2A medium but the microorganism culture appears yellow when grown in nutrient broth. Twitching motility is evidenced on twitching plates, and flagellar motility is evidenced by growth on flagella plates. In addition, this organism can utilize the following: lactate, vanillin, chlorobenzene, ethylbenzene, cyanuric acid, salicylate, and succinate as a sole source of carbon and energy. DAP 119 is further characterized as shown in Table 8.

TABLE 8

| DIFFERENTIAL CHARACTERISTIC | RESULT |
|---|---|
| CATALASE/OXIDASE | (+)/(+) |
| CITRATE UTILIZATION | (+) |
| TRIPLE SUGAR IRON AGAR | $H_2S$ is produced acid and gas from glucose |
| GROWTH AT: | |
| 15° | (+) |
| 25° | (+) |
| 35° | (+) |
| 41° | (+) |
| UTILIZATION OF: | |
| GLUCOSE | (+) |

TABLE 8-continued

| DIFFERENTIAL CHARACTERISTIC | RESULT |
|---|---|
| FRUCTOSE | (+) |
| LACTOSE | (+) |
| MANNITOL | (+) |
| MANNOSE | (+) |
| 2-METHYLNAPHTRALENE | (−) |
| α-KETOGLUTARATE | (+) |
| GLYOXYLATE | (+) |
| GLUTAMATE | (+) |
| ETHANOL | (+) |
| HEXADECANE | (−) |
| $NO_3 \rightarrow NO_2$ | (+) |
| ARGININE DECARBOXYLASE | (+) |
| LYSINE DECARBOXYLASE | (+) |
| ORNITHINE DECARBOXYLASE | (+) |
| GELATIN HYDROLYSI S | (+) |
| UREASE | (+) |
| ANTIBIOTIC RESISTANCE: | |
| $HgCl_2$ | R |
| AMPICILLIN | R |
| KANAMYCIN | R |
| NEOMYCIN | R |
| TETRACYCLINE | R |
| SPECTINOMYCIN | R |
| STREPTOMYCIN | R |

6.1.5 Mixed Microorganism Culture

Over 200 separate pure microorganism isolates were cultured from soil at the collection site. All of these pure isolates, including those described above in Sections 6.1.1 through 6.1.4, were combined and cultured, aerobically, with a sludge/waste material containing a mixture of aromatic, nitro-aromatic, halo-aromatic, aliphatic and halo-aliphatic compounds. A mixed culture of microorganisms was recovered from the cultured material and has been maintained on BACTO™ R2A medium (Difco, Detroit, Mich.).

The mixed culture designated DAP-2, aerobically degrades at least the following compounds or mixtures thereof: benzene, toluene, xylene, ethylbenzene, naphthalene, chlorobenzene, phenol, cresol, nitrobenzene, aniline, anthracene, dimethylphenol, styrene, halonaphthalene, 2-, 3- or 4-chlorotoluene, 2-, 3- or 4-chlorobenzoate, 1,3-dichlorobenzoate, 1,2-, 1,3- or 1,4-dinitrobenzene, 1-chloro-3-nitrobenzene, 1-chloro-4-nitrobenzene, 1- or 2-methylnaphthalene, pyrene, acenaphthylene, fluoranthene, phenanthrene, benzo-(b)-fluoranthene, dibenzofuran, chrysene, catechol, m-toluic acid, cinnamyl acetate, vanillin, trans-cinnamaldehyde, mesitylene, salicylate, melamine, cyanuric acid, δ-(−)-limonene, hexadecane, methanol, formaldehyde, and chloroform.

6.1.5.1. Pure Isolates From the Mixed Culture

The following pure cultures were isolated and identified from the mixed culture designated DAP 2 by isolating single colonies on BACTO™ R2A medium supplemented with 150 ppm each of nitrobenzene, naphthalene, and toluene.

Microorganism DAP 623

DAP 623 is a Gram negative motile rod, generally small single rods, though some pairs are seen. Staining can be uneven and there is some floc formation. The colonies appear white to creamy on BACTO™ R2A medium. In addition, this organism can utilize the following: mesitylene, lactate, succinate, limonene, m-toluic acid, chlorobenzene, salicylate, 2-, 3-, and 4-chlorotoluene, 2-, 3-, and 4-chlorobenzoic acid, and 1,3-dichlorobenzene as a sole source of carbon and energy. DAP 623 is further characterized as shown in Table 8A.

TABLE 8A

| DIFFERENTIAL CHARACTERISTIC | RESULT |
| --- | --- |
| CATALASE/OXIDASE | (+)/(−) |
| CITRATE UTILIZATION | (+) |
| TRIPLE SUGAR IRON AGAR | acid from glucose |
| GROWTH AT: | |
| 15° | (+) |
| 25° | (+) |
| 35° | (+) |
| 41° | (+) |
| UTILIZATION OF: | |
| GLUCOSE | (+) |
| FRUCTOSE | (+) |
| LACTOSE | (−) |
| MANNITOL | (+) |
| MANNOSE | (+) |
| 2-METHYLNAPHTHALENE | (−) |
| α-KETOGLUTARATE | (+) |
| GLUTAMATE | (+) |
| ETHANOL | (−) |
| HEXADECANE | (−) |
| $NO_3 \rightarrow NO_2$ | (+) |
| ARGININE DECARBOXYLASE | (+) |
| LYSINE DECARBOXYLASE | (+) |
| ORNITHINE DECARBOXYLASE | |
| GELATIN HYDROLYSIS | (+) |
| UREASE | (+) |
| ANTIBIOTIC RESISTANCE: | |
| $HgCl_2$ | (−) |
| AMPICILLIN | R |
| KANAMYCIN | (−) |
| TETRACYCLINE | R |
| SPECTINOMYCIN | R |
| STREPTOMYCIN | (−) |

Microorganism DAP 626

DAP 626 is a Gram variable rod which vary in size and occur singly and in pairs. Growth on flagella plates is seen which indicates flagellar motility. In addition, this organism can utilize the following: mesitylene, lactate, succinate, limonene, cinnamyl acetate, catechol, m-toluic acid, chlorobenzene, 2-, 3-, and 4-chlorotoluene, 2-, 3-, and 4-chlorobenzoic acid, and 1,3-dichlorobenzene as a sole source of carbon and energy. DAP 626 is further characterized as shown in Table 8B.

TABLE 8B

| DIFFERENTIAL CHARACTERISTIC | RESULT |
| --- | --- |
| CATALASE/OXIDASE | (+)/(+) |
| CITRATE UTILIZATION | (−) |
| TRIPLE SUGAR IRON AGAR | $H_2S$ is produced |
| GROWTH AT: | |
| 15° | (+) |
| 25° | (+) |
| 35° | (+) |
| 41° | (+) |
| UTILIZATION OF: | |
| GLUCOSE | (−) |
| FRUCTOSE | (+) |
| LACTOSE | (−) |
| MANNITOL | (+) |
| MANNOSE | (−) |

TABLE 8B-continued

| DIFFERENTIAL CHARACTERISTIC | RESULT |
| --- | --- |
| 2-METHYLNAPHTHALENE | (−) |
| α-KETOGLUTARATE | (+) |
| GLUTAMATE | (+) |
| ETHANOL | (+) |
| HEXADECANE | (+) |
| $NO_3 \rightarrow NO_2$ | (−) |
| ARGININE DECARBOXYLASE | (−) |
| LYSINE DECARBOXYLASE | (−) |
| ORNITHINE DECARBOXYLASE | (−) |
| GELATIN HYDROLYSIS | (−) |
| UREASE | (+) |
| ANTIBIOTIC RESISTANCE: | |
| $HgCl_2$ | (−) |
| AMPICILLIN | R |
| KANAMYCIN | (−) |
| SPECTINOMYCIN | (−) |
| STREPTOMYCIN | R |

Microorganism DAP 629

DAP 629 is a Gram negative small motile rod, almost cocco-bacillary. Colonies appeared white with a slight fluorescence when grown on BACTO™ R2A agar. In addition, this organism can utilize the following: fluoranthrene, mesitylene, lactate, succinate, limonene, m-toluic acid, chlorobenzene, 2-, 3-, and 4-chlorotoluene, 2-, 3-, and 4-chlorobenzoic acid, and 1,3-dichlorobenzene as a sole source of carbon and energy. DAP 626 is further characterized as shown in Table 8C.

TABLE 8C

| DIFFERENTIAL CHARACTERISTIC | RESULT |
| --- | --- |
| CATALASE/OXIDASE | (+)/(+) |
| CITRATE UTILIZATION | (−) |
| TRIPLE SUGAR IRON AGAR | no fermentation |
| GROWTH AT: | |
| 15° | (+) |
| 25° | (+) |
| 35° | (+) |
| 41° | (−) |
| UTILIZATION OF: | |
| GLUCOSE | (+) |
| FRUCTOSE | (−) |
| LACTOSE | (−) |
| MANNITOL | (−) |
| MANNOSE | (−) |
| 2-METHYLNAPHTHALENE | (−) |
| α-KETOGLUTARATE | (+) |
| GLUTAMATE | (+) |
| ETHANOL | (−) |
| HEXADECANE | (−) |
| $NO_3 \rightarrow NO_2$ | (+) |
| ARGININE DECARBOXYLASE | (−) |
| LYSINE DECARBOXYLASE | (+) |
| ORNITHINE DECARBOXYLASE | (−) |
| GELATIN HYDROLYSIS | (+) |
| UREASE | |
| ANTIBIOTIC RESISTANCE: | |
| $HgCl_2$ | (−) |
| AMPICILLIN | R |
| KANAMYCIN | (−) |
| TETRACYCLINE | (−) |
| SPECTINOMYCIN | (−) |
| STREPTOMYCIN | (−) |

Microorganism DAP 632

DAP 632 is a Gram variable motile slender rod, seen both singly and in pairs. Colonies appeared creamy to yellowish when grown on BACTO™ R2A agar. In addition, this organism can utilize the following: fluoranthrene, acenaphthalene, mesitylene, lactate, limonene, m-toluic acid, chlorobenzene, 2-, 3-, and 4-chlorotoluene, 2-, 3-, and 4-chlorobenzoic acid, and 1,3-dichlorobenzene as a sole source of carbon and energy. DAP 626 is further characterized as shown in Table 8D.

TABLE 8D

| DIFFERENTIAL CHARACTERISTIC | RESULT |
|---|---|
| CATALASE/OXIDASE | (+)/(-) |
| CITRATE UTILIZATION | (+) |
| TRIPLE SUGAR IRON AGAR | no fermentation |
| GROWTH AT: | |
| 15° | (+) |
| 25° | (+) |
| 35° | (+) |
| 41° | (+) |
| UTILIZATION OF: | |
| GLUCOSE | (-) |
| FRUCTOSE | (-) |
| LACTOSE | (-) |
| MANNITOL | (-) |
| MANNOSE | (-) |
| 2-METHYLNAPHTHALENE | (-) |
| α-KETOGLUTARATE | (-) |
| GLUTAMATE | (+) |
| ETHANOL | (-) |
| HEXADECANE | (-) |
| $NO_3 \rightarrow NO_2$ | (-) |
| ARGININE DECARBOXYLASE | (-) |
| LYSINE DECARBOXYLASE | (-) |
| ORNITHINE DECARBOXYLASE | (-) |
| GELATIN HYDROLYSIS | (+) |
| UREASE | (+) |
| ANTIBIOTIC RESISTANCE: | |
| $HgCl_2$ | R |
| AMPICILLIN | R |
| KANAMYCIN | R |
| TETRACYCLINE | R |
| SPECTINOMYCIN | R |
| STREPTOMYCIN | R |

Microorganism DAP 115

DAP 115 is a Gram negative motile rod. Growth is observed on flagella plates, indicating motility is flagellar. Colonies appeared white when grown on BACTO™ R2A agar, but appear yellow in nutrient broth. In addition, this organism can utilize the following: benzo-(b)-fluoranthrene, fluoranthrene, dibenzofuran, acenaphthalene, salicylate, lactate, succinate, glyoxylate, mesitylene, vanillin, limonene, cinnamyl acetate, catechol, m-toluic acid, chlorobenzene, 2-, 3-, and 4-chlorotoluene, 2-, 3-, and 4-chlorobenzoic acid, and 1,3-dichlorobenzene as a sole source of carbon and energy. DAP 115 is further characterized as shown in Table 8E.

TABLE 8E

| DIFFERENTIAL CHARACTERISTIC | RESULT |
|---|---|
| CATALASE/OXIDASE | (+)/(+) |
| CITRATE UTILIZATION | (+) |
| TRIPLE SUGARIRON AGAR | $H_2S$ is produced acid and gas from glucose |
| GROWTH AT: | |
| 15° | (+/-) |
| 25° | (+) |

TABLE 8E-continued

| DIFFERENTIAL CHARACTERISTIC | RESULT |
|---|---|
| 35° | (+) |
| 41° | (+) |
| UTILIZATION OF: | |
| GLUCOSE | (+) |
| FRUCTOSE | (+) |
| LACTOSE | (-) |
| MANNITOL | (+) |
| MANNOSE | (+) |
| 2-METHYLNAPHTHALENE | (+) |
| α-KETOGLUTARATE | (+) |
| GLUTAMATE | (+) |
| ETHANOL | (-) |
| HEXADECANE | (+) |
| $NO_3 \rightarrow NO_2$ | (+) |
| ARGININE DECARBOXYLASE | (-) |
| LYSINE DECARBOXYLASE | (-) |
| ORNITHINE DECARBOXYLASE | (+) |
| GELATIN HYDROLYSIS | (+) |
| UREASE | (+) |
| ANTIBIOTIC RESISTANCE: | |
| $HgCl_2$ | R |
| AMPICILLIN | R |
| KANAMYCIN | R |
| TETRACYCLINE | R |
| SPECTINOMYCIN | R |
| STREPTOMYCIN | R |

Microorganism DAP 120

DAP 120 is a Gram negative motile rod. Growth is observed on flagella plates, indicating motility is flagellar. In addition, this organism can utilize the following: chrysene, pyrene, lactate, succinate, glyoxylate, salicylate, mesitylene, vanillin, limonene, cinnamyl acetate, catechol, m-toluic acid, chlorobenzene, 2-, 3-, and 4-chlorotoluene, 2-,3-, and 4-chlorobenzoic acid, and 1,3-dichlorobenzene as a sole source of carbon and energy. DAP 120 is further characterized as shown in Table 8F.

TABLE 8F

| DIFFERENTIAL CHARACTERISTIC | RESULT |
|---|---|
| CATALASE/OXIDASE | (+)/(+) |
| CITRATE UTILIZATION | (+) |
| TRIPLE SUGAR IRON AGAR | $H_2S$ is produced |
| GROWTH AT: | |
| 15° | (+) |
| 25° | (+) |
| 35° | (+) |
| 41° | (+) |
| UTILIZATION OF: | |
| GLUCOSE | (+) |
| FRUCTOSE | (+) |
| LACTOSE | (-) |
| MANNITOL | (+) |
| MANNOSE | (-) |
| 2-METHYLNAPHTHALENE | (+) |
| α-KETOGLUTARATE | (+) |
| GLUTAMATE | (+) |
| ETHANOL | (-) |
| HEXADECANE | (+) |
| $NO_3 \rightarrow NO_2$ | (+) |
| ARGININE DECARBOXYLASE | (-) |
| LYSINE DECARBOXYLASE | (-) |
| ORNITHINE DECARBOXYLASE | (-) |
| GELATIN HYDROLYSIS | (+) |
| UREASE | (+) |

TABLE 8F-continued

| DIFFERENTIAL CHARACTERISTIC | RESULT |
|---|---|
| ANTIBIOTIC RESISTANCE: | |
| $HgCl_2$ | R |
| AMPICILLIN | R |
| KANAMYCIN | R |
| TETRACYCLINE | R |
| SPECTINOMYCIN | (−) |
| STREPTOMYCIN | (−) |

The following Table 8G shows that the above-described pure cultures, isolated from the mixed culture designated DAP 2, are able to grow solely on Stanier's minimal medium supplemented with 150 ppm each of nitrobenzene, naphthalene, and toluene. The cultures were grown at 25°–27° C., colony size determined after 14 days. Values represent mean of five replicate colonies for each determination.

TABLE 8G

| CULTURE | GROWTH* | COLONY SIZE |
|---|---|---|
| DAP 626 | ++ | 3.8 mm |
| DAP 115 | ++/+++ | 5.0 mm |
| DAP 632 | ++/+++ | 4.7 mm |
| DAP 623 | ++ | 4.0 mm |
| DAP 120 | +/++[a] | a |
| DAP 629 | ++ | 4.3 mm |

*Growth scored as ++++ luxuriant, +++ good, ++ fair, + modest, +/− scant, − no growth
[a]Growth of strain DAP 120 was very thin but rapidly spreading, therefore, precise quantitation was not possible.

The following Table 8H shows that the above-described pure cultures, isolated from the mixed culture designated DAP 2, are able to utilize melamine as a source of nitrogen as determined by colony size of cultures. The cultures were grown on Stanier's minimal medium supplemented with 150 ppm each of naphthalene and toluene and 25 ppm of melamine as either the sole source of nitrogen or supplemented with ammonium sulfate, $(NH_4)_2SO_4$. The cultures were grown at 25°–27° C., colony size determined after 7 days. Values represent mean of five replicate colonies for each determination.

TABLE 8H

| CULTURE | WITH $(NH_4)_2SO_4$ | WITHOUT $(NH_4)_2SO_4$ |
|---|---|---|
| DAP 626 | 3.2 mm | 4.2 mm |
| DAP 115 | 5.2 mm | 4.6 mm |
| DAP 632 | 4.9 mm | 4.7 mm |
| DAP 623 | 4.1 mm | 6.0 mm |
| DAP 120 | 4.3 mm | 4.5 mm |
| DAP 629 | 3.9 mm | 3.8 mm |

6.1.6 Microorganisms Which Cannot Degrade Nitrobenzene

A number of microorganisms were isolated from sludges or soils containing nitrobenzene and tested for the ability to aerobically degrade this compound. The following strains were identified which could not degrade nitrobenzene: (1) *Pseudomonas* sp. DN-1081; (2) *Pseudomonas* sp. DN-1101-1; (3) *Pseudomonas* sp DN-1018; (4) *Pseudomonas* sp. DN-1019; (5) *Pseudomonas* sp. DR-1111-1; and (6) *Pseudomonas* sp. DR-1111-2.

6.2. Methods For Aerobic Degradation of Compounds

According to one embodiment of the present invention, a method for the aerobic degradation of aromatic and/or substituted aromatic compounds is provided. In general, the method entails contacting an aromatic compound with a mixed or pure culture of microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. In one mode of this embodiment, at least one compound selected from the group of aromatic, nitro-aromatic, halo-aromatic, halo-nitro-aromatic, aliphatic and halo-aliphatic compounds is aerobically degraded. In another mode of this embodiment, a mixture of at least two compounds selected from the group consisting of aromatic, nitro-aromatic, halo-aromatic, halo-nitro-aromatic, aliphatic and halo-aliphatic compounds is aerobically degraded. The method may further comprise culturing the microorganisms in contact with said compound(s) so that the aromatic compound or compounds are degraded to products comprising $CO_2$ and $H_2O$. According to yet another embodiment of the invention, the method entails using a microorganism selected from the group consisting of microorganisms having ATCC Accession No. 55644, 55648, 55645, 55641, 55647, 55642, 55643, 55646, 55649, 55722, 55723, 55726, 55727, 55724, and 55725 to degrade at least one aromatic, nitro-aromatic, halo-aromatic and/or halo-nitro-aromatic compound at a total concentration of about 10 ppm to 100,000 ppm to products comprising $CO_2$ and $H_2O$ in about 2 to 72 hours.

In a preferred embodiment, if for example, nitrogen containing aromatic compounds are present, they are degraded to products comprising $CO_2$ and $H_2O$ and nitrogen containing compounds which pose little or no threat to the biosphere.

As mentioned above herein, the aromatic, nitro-aromatic, halo-aromatic, halo-nitro-aromatic, aliphatic and halo-aliphatic compounds which are degraded according to the present invention, include but are not limited to compounds such as benzene, toluene, xylene, ethylbenzene, naphthalene, chlorobenzene, phenol, cresol, nitrobenzene, aniline, anthracene, dimethylphenol, styrene, halonaphthalene, 2-, 3- or 4-chlorotoluene, 2-, 3- or 4-chlorobenzoate, 1,3-dichlorobenzoate, 1,2-, 1,3- or 1,4-dinitrobenzene, 1-chloro-3-nitrobenzene, 1-chloro-4-nitrobenzene, 1- or 2-methylnaphthalene, pyrene, acenaphthylene, fluoranthene, phenanthrene, benzo-(b)-fluoranthene, dibenzofuran, chrysene, catechol, m-toluic acid, cinnamyl acetate, vanillin, trans-cinnamaldehyde, melamine, cyanuric acid, mesitylene, and salicylate.

According to another embodiment of the present invention, a method for the aerobic degradation of aliphatic compounds is provided. These aliphatic compounds include but are not limited to δ-(−)-limonene, hexadecane, methanol, formaldehyde and chloroform. In general, the method entails contacting said aliphatic or halo-aliphatic compounds or a mixture of said compounds with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. The method may further comprise culturing said microorganisms in contact with said compound or mixture of compounds such that said compound or mixture thereof is degraded to products comprising $CO_2$ and $H_2O$.

The microorganisms can degrade high levels of the compounds to be degraded, such that high levels do not interfere with actual degradation.

These methods may further comprise monitoring the removal of the aromatic or aliphatic compound or compounds of interest. For example, measurements of oxygen uptake or carbon dioxide evolution can be used to monitor the degradation of the compound or compounds of interest. In addition, the pH and/or buffering capacity is useful to assess the level of biological activity.

The compounds to be degraded may be in solid, liquid, and/or gaseous form. When a compound is in the gaseous and/or liquid form, it may be sorbed onto a material, such as a solid.

Ideally, when the method entails a culture of the microorganisms, culture conditions should be such that bacterial growth is supported, for example, pH between 3.0 and 11.0, preferably between 6.0 and 8.0; temperature between 4° C. and 41° C., preferably between 15° C. and 37° C.; dissolved oxygen tension between 0.1% and 100%, preferably between 4% and 80%, more preferably between 4% and 40% of saturation where the oxygen may be supplied by use of an oxygen containing or oxygen liberating composition. The oxygen containing or oxygen liberating composition can be air, pure oxygen, peroxide, or other peroxy chemicals which liberate oxygen or mixtures thereof.

Further, the culture medium may be stirred or may not be stirred, provided with positive dissolved oxygen tension or not, and supplemental nutrients may or may not be added to maintain an optimal Carbon:Nitrogen:Phosphorous ratio between 10:1:0.1 and 50:1:1, preferably 25:1:0.1. In a preferred mode, only carbon is limiting for bacterial growth.

Any method for contacting the microorganisms with a composition containing any one or more of the above recited compounds or mixtures thereof can be used according to the present invention. Such methods for contact include but are not limited to in situ contact, for example, at a site contaminated with such compound or mixture thereof, contact in a closed vessel or container, etc.

6.3. Fluid Phase System for Aerobic Reaction of Compounds

According to another embodiment of the invention, fluid phase systems and methods for aerobic reaction of compounds are provided. Most generally, the fluid phase systems entail converting an elastomeric solid or sludge into a fluidized composition suitable for aerobic reaction of organic compounds contained in the elastomeric solid or sludge. The aerobic reactions for which the fluidized compositions are useful include synthetic as well as degradative reactions which take place preferably under aerobic conditions.

The method for preparing a fluidized composition suitable for aerobic reaction comprises the steps of: (a) particularizing an elastomeric solid or sludge containing an organic compound; and (b) contacting the particularized solid or sludge in a vessel with a current of fluid selected from the group consisting of oxygen, oxygen containing gas, including air, water and an aqueous solution, such that the particularized solid or sludge is suspended in the current of fluid to form a fluidized composition suitable for aerobic reaction of an organic compound contained in the solid or sludge.

The elastomeric solid or sludge can be particularized by mixing the elastomeric solid or sludge, for example, in a pug mill, a plow-bladed mixer or a screw mixer. The size of the particularized material will vary depending upon a number of factors, including such as the size of the blades of the mill or mixer, the clearance between the blades and the mill or mixer wall, the amount of detackifying agent, if added, and the degree and rate of mixing.

The method can further comprise combining the elastomeric solid or sludge with a detackifying agent either simultaneously with or subsequent to step (a). In one embodiment, the detackifying agent is selected from the group consisting of clays, chopped, minced or otherwise finely divided organic materials, powdered inorganic salts and rock dust. In an alternative embodiment, the detackifying agent is selected from the group consisting of pulverized lime, portland cement, bentonite clay, sawdust, diatomaceous earth, pulverized corn cobs and mixtures thereof. The range of detackifying agent that can be used is from about 2–100% (w/w).

In a particular mode of this embodiment of the invention, the fluidized composition is used to partially convert an aromatic compound to a cis—cis muconate which is useful for the preparation of useful polymers. In an alternative particular mode of this embodiment of the invention, the fluidized composition comprises a composition containing hydrocarbons such as naval stores, e.g. α-pinene and/or β-pinene, and a detackifying agent. The fluidized composition is used as an oxygenated fuel which advantageously results in a cleaner burning fuel.

In a different particular mode of this embodiment of the invention, the fluidized composition is used for a reaction which comprises aerobic degradation of an organic compound selected from the group consisting of aromatic, nitro-aromatic, halo-aromatic, halo-nitro-aromatic, aliphatic and halo-aliphatic compounds. For example, a fluidized composition comprising a particularized sludge, containing nitrobenzene, suspended in a current of water or an aqueous solution is contacted under aerobic conditions with microorganisms selected from the group of microorganisms have ATCC Accession No. 55644, 55648, 55645, 55641, 55647, 55642, 55643, 55646, 55649, 55722, 55723, 55726, 55727, 55724, and 55725, so that the nitrobenzene in the fluidized compositions is degraded to products comprising $CO_2$ and $H_2O$. FIG. 1$b$ is an illustrative schematic of one fluid phase system useful for the methods of the invention. This illustrates a system for imparting energy in the form of mechanical energy to form the slurry.

According to another embodiment of the present invention fluid phase systems and methods for aerobic degradation of compounds are provided. A fluid phase which is a slurry formed from, for example, a solid, soil, and/or sludge is produced. The slurries are used, for example for treatment of aromatic, nitro-aromatic, halo-aromatic, halo-nitro-aromatic, aliphatic or halo-aliphatic compounds in solids, soils and/or sludges with microorganisms which can act on such compounds.

A fluid phase which is a slurry can be formed from either non-elastomeric or an elastomeric solid, sludge or soil. Such slurries are used to aerobically degrade an aromatic or aliphatic compound or mixture thereof contained in said solid, sludge or soil.

The preparation of slurries, according to the present invention, using elastomeric solids, sludge and/or soils is particularly advantageous for the aerobic degradation of aromatic or aliphatic compounds contained in such compositions using the microorganisms disclosed in this application.

The preparation of slurries as well as systems and methods for the aerobic degradation, by microorganisms, using the slurries is described in the following sub-sections.

6.3.1. Formation of Slurry Phases

Figure 2A:
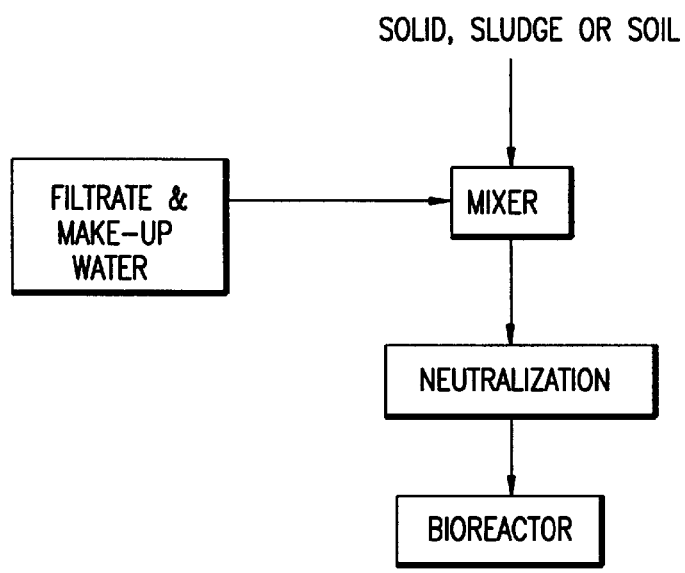
FIG. 2a. Formation of a slurry phase from a non-elastomeric solid, sludge or soil.
Figure 2B:
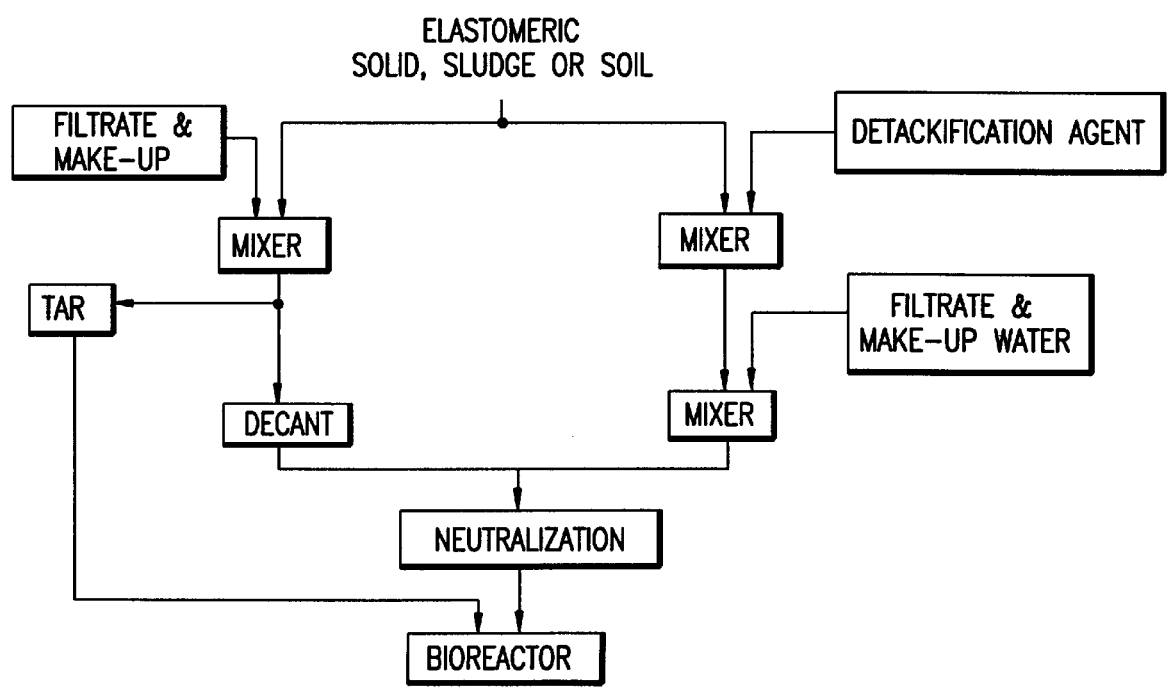
FIG. 2b. Formation of a slurry phase from an elastomeric solid, sludge or soil.

The formation of slurry phases useful according to this embodiment is illustrated schematically in FIGS. 2a–b. FIG. 2a illustrates the formation of a slurry using a non-elastomeric solid, sludge or soil. The method comprises (a) combining said solid or sludge with water or an aqueous solution; and (b) imparting energy to said solid or sludge/aqueous combination in a vessel such that said solid or sludge is fluidized into a slurry.

Energy can be imparted, for example, by imparting mechanical energy, e.g., by mixing; by imparting acoustic energy; e.g., by setting up a standing acoustic wave in the slurry materials; or by imparting an electrical or electrostatic field. FIG. 1a also illustrates one exemplary mode of the invention in which mechanical energy is imparted for example, by mixing.

As illustrated in FIG. 2a, the pH of said slurry can be adjusted towards neutrality, if necessary, for example, if the slurry is to be contacted with microorganisms to degrade a compound or mixture of compounds in said slurry.

FIG. 2b illustrates the formation of a slurry from an elastomeric solid, sludge or soil. In one alternative embodiment, the method comprises (a) combining an elastomeric solid or sludge with water or an aqueous solution; (b) imparting energy to said elastomeric solid or sludge/water combination such that said solid or sludge is fluidized into a slurry; and (c) separating said slurry away from any residual elastomeric solid or sludge. Separation can be accomplished, for example, by decanting the slurry from residual elastomer. Alternatively, the method comprises (a) combining an elastomeric solid or sludge with a detackifying agent to form a solid or sludge/detackifying agent combination; (b) combining said solid or sludge/detackifying agent combination with water or an aqueous solution; and (c) imparting energy to said solid or sludge/detackifying agent aqueous combination such that said detackified solid or sludge is fluidized into a slurry. The method can further comprise mixing said solid or sludge/detackifying agent combination to form a detackified solid or sludge. In still another alternative, the method comprises (a) combining an elastomeric solid or sludge with a detackifying agent and water or an aqueous solution; and (b) imparting energy to said mixture formed in step (a) such that said elastomeric solid or sludge is fluidized into a slurry.

Energy can be imparted, for example, by imparting mechanical energy, e.g., by mixing; by imparting acoustic energy; e.g., by setting up a standing acoustic wave in the slurry materials; or by imparting an electrical or electrostatic field. FIG. 1a illustrates one exemplary mode of the invention in which mechanical energy is imparted for example, by mixing.

Suitable detackifying agents for producing a slurry according to the invention include but are not limited to clays, chopped, minced or otherwise finely divided organic materials, powdered inorganic salts and rock dust. Additional suitable detackifying agents include pulverized lime, portland cement, bentonite clay, sawdust, diatomaceous earth, pulverized corn cobs and mixtures thereof.

The aqueous solution used to make a slurry of the invention can be the filtrate from a previously conducted slurry phase bioremediation as described herein.

As illustrated in FIG. 2b, any of the alternative embodiments described above can further comprise adjusting the pH of said slurry towards neutrality, if desired.

The above described methods for forming a slurry phase from an elastomeric solid, sludge or soil containing an aromatic or aliphatic compound or mixture thereof are particularly advantageous because such slurries, which can comprise about 45% (w/w) of the original elastomeric solid or sludge are useful in fluid phase methods for aerobic degradation of said compounds or mixtures thereof. Prior to the present invention, slurry phase treatments of such elastomeric materials were not possible.

Thus, the slurries are useful for bioremediation processes in which aromatic, nitro-aromatic, halo-aromatic, halo-nitro-aromatic, aliphatic or halo-aliphatic compound(s) or a mixture thereof contained in a solid, sludge, soil or other waste material are treated aerobically.

If volatile compounds are present in the solid, sludge, soil or other waste material, they may be stripped from the material while under going mixing with a detackifying agent. Accordingly, such steps should be carried out in such a way that the volatiles are trapped, for example, in a biofilter. Once trapped in a biofilter, the volatiles can be treated with microorganisms as described infra in Section 6.5.

6.3.2. Microorganisms/Inoculum For Slurry Phase Degradation

A pure culture of microorganisms or a mixed culture of microorganisms selected from those described in Section 6.1 above is used as inoculum for the slurry phase methods. The microorganisms used are selected based on their ability to degrade a desired compound or mixture of compounds present in a particular slurry aerobically.

The microorganisms are induced as described in Section 6.1 above, for example, by culturing them on a medium, which contains as the sole source of nutrients the compound (s) one wishes to degrade.

Alternatively, residual solids from a previously performed slurry phase bioremediation, which contains already induced microorganisms, can be used as inoculum for the slurry phase methods. For example, after a slurry has been bioremediated, it can be filtered. The filtrate can be used for producing more slurry and the dewatered residual solid residue, designated "filter cake", containing already induced microorganisms, is added to a slurry to be bioremediated.

When using filter cake as the source of mixed culture inoculum, between 200–600 grams of filter cake, and preferably between 350–450 grams of filter cake are used, for example, to start a 4 liter batch. Once the aromatic or aliphatic compound or mixture thereof has been degraded, the contents of a 4 liter batch can be used as the source of inoculum for a 10 gallon batch, and this in turn can be used to initiate a 150 gallon batch. This technique can be extended and extrapolated to build up an inoculum for increasingly larger reactors.

If filter cake is not available, the inoculum can be re-established by using preserved cultures of the microorganisms described in Section 6.1.1 through 6.1.4 to inoculate several plates per preserved culture. The plates containing Stanier's minimal medium supplemented with appropriate hydrocarbon(s) are then incubated at 25° C. When the cultures have grown, the plates are washed with 5–10 ml of Stanier's minimal medium. The washes are pooled and used to inoculate a series of biphasic flasks with medium supplemented with agar and the appropriate hydrocarbon(s), and 50 ml of liquid medium of the same composition. After the microorganism inoculated in the biphasic flasks has grown-up, the surface of the agar layer is scraped to remove cells. The liquid layer from 4 flasks is used to inoculate a four liter vessel. From this point, further scale-up is identical to that employed when filter cake is used as the source of inoculum.

6.3.3. Slurry Phase Methods and Biotreatment Parameters

According to the present invention, a method for slurry phase bioremediation of solids, sludges or soils containing at least one compound or a mixture of at least two compounds selected from the group consisting of aromatic, nitro-aromatic, halo-aromatic, halo-nitro-aromatic, aliphatic and halo-aliphatic compounds comprises (a) adjusting the pH of a slurry towards neutrality, if necessary; and (b) contacting said neutral slurry with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. The method can further comprise culturing said microorganisms with said slurry such that the compound is degraded to products comprising $CO_2$ and $H_2O$. The method can be accomplished in a vessel, such as bioreactor.

Another method for the slurry phase bioremediation of solids, sludges or soils containing at least one compound or a mixture of at least two compounds selected from the group consisting of aromatic, nitro-aromatic, halo-aromatic, halo-nitro-aromatic, aliphatic and halo-aliphatic compounds comprises (a) combining said solid or sludge with water or an aqueous solution; (b) imparting energy to said solid or sludge/aqueous combination in a vessel such that said solid or sludge is fluidized into a slurry; (c) adjusting the pH of said slurry, if necessary; and (d) contacting said neutral slurry with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. Energy can be imparted using any of the methods mentioned about in Section 6.3.1 for forming a slurry. The method can further comprise culturing said microorganisms with said slurry such that the compound is degraded to products comprising $CO_2$ and $H_2O$.

If the solid, sludge or soil is a tarry or elastomeric solid, sludge or soil the method comprises (a) combining said solid or sludge with water or an aqueous solution; (b) imparting energy to said solid or sludge/aqueous combination in a vessel such that said solid or sludge is fluidized into a slurry; (c) separating said slurry from any residual elastomeric solid or sludge; (d) adjusting the pH of said slurry, if necessary; and (e) contacting said neutral slurry with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. Energy can be imparted using any of the methods mentioned above in Section 6.3.1 for forming a slurry. Further, the method can also comprise gradually adding the residual elastomeric solid or sludge to the neutral slurry in contact with said microorganisms in step (e).

If the solid, sludge or soil to be treated in slurry phase is a tarry or elastomeric solid, sludge or soil containing at least one compound or a mixture of compounds selected from the group consisting of aromatic, nitro-aromatic, halo-aromatic, halo-nitro-aromatic, aliphatic and halo-aliphatic compounds the method, alternatively, comprises (a) combining said elastomeric solid or sludge with a detackifying agent; (b) mixing said solid or sludge/detackifying agent combination to form a detackified solid or sludge; (c) combining said detackified solid or sludge with water or an aqueous solution; (d) imparting energy to said detackified solid or sludge such that said detackified solid or sludge is fluidized into a slurry; (e) adjusting the pH of said slurry towards neutrality, if necessary; and (f) contacting said neutral slurry with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. Energy can be imparted using any of the methods mentioned about in Section 6.3.1 for forming a slurry. This method can further comprise culturing said microorganisms with said slurry such that the compound is degraded to products comprising $CO_2$ and $H_2O$.

Another method for the slurry phase bioremediation of a solid, sludge or soil where the solid, sludge or soil is a tarry or elastomeric solid, sludge or soil containing at least one compound or a mixture of compounds selected from the group consisting of aromatic, nitro-aromatic, halo-aromatic, halo-nitro-aromatic, aliphatic and halo-aliphatic compounds comprises (a) combining an elastomeric solid, sludge or soil with a detackifying agent and water or an aqueous solution to form a mixture; (b) imparting energy to said mixture formed in step (a) such that said elastomeric solid, sludge or soil is fluidized into a slurry; (c) adjusting the pH of said slurry towards neutrality, if necessary; and (d) contacting said neutral slurry with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. Energy can be imparted using any of the methods mentioned above in Section 6.3.1 for forming a slurry. The method can further comprise culturing said microorganisms with said slurry such that the compound is degraded to products comprising $CO_2$ and $H_2O$.

In any of the above methods, the tarry or elastomeric solid, sludge or soil may be residual elastomeric solid, sludge or soil formed as described according to the methods of the invention. In each case the residual elastomeric solid, sludge or tar may contain a very high concentration of compounds which can be effectively degraded according to the methods of the present invention.

In one embodiment, the compound contained in the solid, sludge, soil or other waste material is selected from benzene, toluene, xylene, ethylbenzene, naphthalene, chlorobenzene, phenol, cresol, nitrobenzene, aniline, anthracene, dimethylphenol, styrene, halonaphthalene, 2-, 3- or 4-chlorotoluene, 2-, 3- or 4-chlorobenzoate, 1,3-dichlorobenzoate, 1,2-, 1,3- or 1,4-dinitrobenzene, 1-chloro-3-nitrobenzene, 1-chloro-4-nitrobenzene, 1- or 2-methylnaphthalene, pyrene, acenaphthylene, fluoranthene, phenanthrene, benzo-(b)-fluoranthene, dibenzofuran, chrysene, catechol, m-toluic acid, cinnamyl acetate, vanillin, trans-cinnamaldehyde, mesitylene, salicylate, melamine, cyanuric acid, δ-(-)-limonene, hexadecane, methanol, formaldehyde, and chloroform or a mixture of said compounds.

Suitable detackifying agents are selected from clays, chopped, minced or otherwise finely divided organic materials, powdered inorganic salts and rock dust. Alternatively, detackifying agents are selected from pulverized lime, portland cement, bentonite clay, sawdust, diatomaceous earth, pulverized corn cobs and mixtures thereof. In another embodiment, the compound is selected from methanol, formaldehyde or chloroform.

According to a preferred embodiment, the detackifying agents are selected from inorganic agents, such as rock dust, diatomaceous earth, etc.

The slurry/microorganism mixture is maintained under conditions which favor the growth of the bacteria and the biodegradation of the desired compound(s). Generally, the conditions should be such that bacterial growth is supported, for example, pH between about 3.0 and 11.0, preferably between 6.0 and 8.0; and temperature between about 4° C. and 41° C., preferably between 15° C. and 37° C. The dissolved oxygen tension should be between about 0.1% and 100%, preferably between 4% and 80%, more preferably between 4% and 30%. The dissolved oxygen tension may be monitored and maintained in the desired range by supplying oxygen in the form of air, pure oxygen, peroxide, and/or other peroxy compositions which liberate oxygen. The mixture may be stirred or may not be stirred, provided with positive dissolved oxygen tension or not, and supplemental nutrients may or may not be added to maintain an optimal Carbon:Nitrogen:Phosphorous ratio between about 10:1:0.1 and 50:1:1, preferably 25:1:0.1, such that only carbon is limiting for bacterial growth. Additionally, a water-soluble, polymeric coagulant/flocculant such as MAGNIFLOC® 591C, a quaternary ammonium cationic polymeric with a molecular weight of about 300 kD to 500 kD (Cytec Industries, West Paterson, N.J.) can be added to improve the filterability and settling characteristics of solids in the slurry phase bioreactor. The settled solids can be used as inoculum for a subsequent bioremediation process.

At different time points one may remove solids or liquids and, for example, extract them with methylene chloride:methanol, (90:10) or by EPA approved methodology for TCLP or TCL, and measure the concentration of selected compound(s) by gas-liquid chromatography.

6.3.4. Modes of Operation

The fluid phase methods for aerobic reaction of compounds of the present invention can be operated in a variety of modes, including batch mode, sequencing batch mode and continuous or semi-continuous mode. Three modes of operation are described in below in terms of modes of operation for slurry phase methods of aerobic degradation of an aromatic or aliphatic compound or mixture thereof; however the modes of operation described below can also be used for the methods for aerobically reacting an organic compound in a fluidized composition as described above.

In all three modes of operation, samples of the contents may be removed periodically to monitor degradation of the compound(s) of interest. Additionally, the agitating and/or mixing of the reactor contents may induce foaming. In these cases, an anti-foaming agent may be added to prevent foaming. Suitable anti-foaming agents include such as silicon containing anti-foam emulsion (e.g., Dow ANTIFOAM-A®; a silicon based anti-foaming agent).

6.3.4.1. Batch Node Operation

Batch mode operation entails placing a slurry containing a compound or mixture of at least two compounds selected from the group consisting aromatic, nitro-aromatic, halo-nitro-aromatic, aliphatic and halo-aliphatic compounds into a vessel, such as a bioreactor, inoculating with induced microorganisms as described in Section 6.1.1 through 6.1.4 and incubating the mixture to culture the microorganisms such that the aromatic or aliphatic compound(s) is (are) degraded. After a predetermined time period, the incubation is stopped and the contents are removed and the solids are separated from the liquid by filtration. Samples may then be taken from both the solid and liquid phase and are tested, for example, by TCLP or by gas-liquid chromatography to assess the level of the compound(s) to confirm that the compound(s) has been degraded. The reactor solids are subsequently dewatered and may be further processed into, for example, a landfill or may be used as bacterial inoculum for the next batch mode. In batch mode the dewatered solid residue is re-added at about 2%–40% by weight or volume, preferably at about 5%-20%. (See, for example FIG. 1c)

Figure 1B:
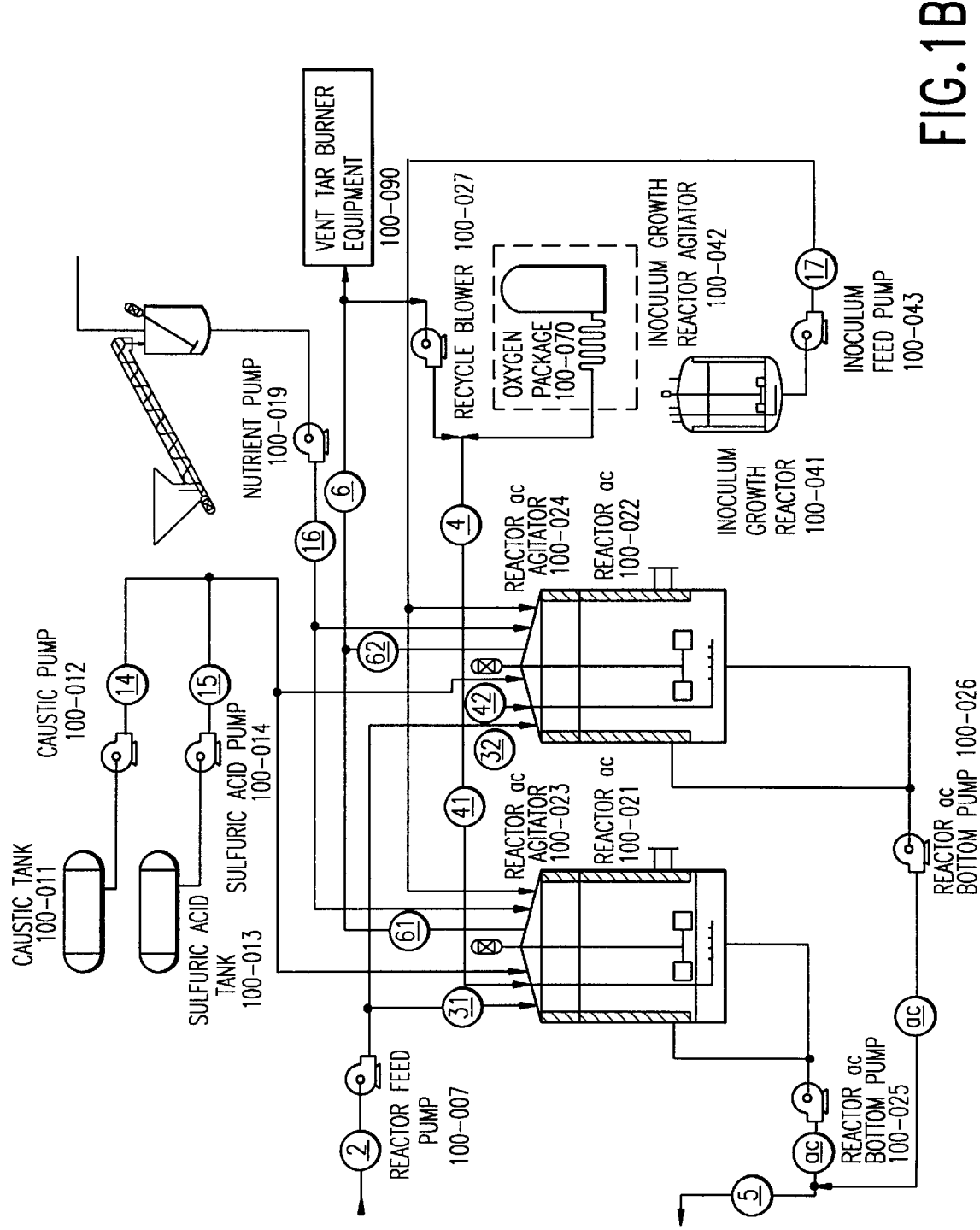
Figure 1C:
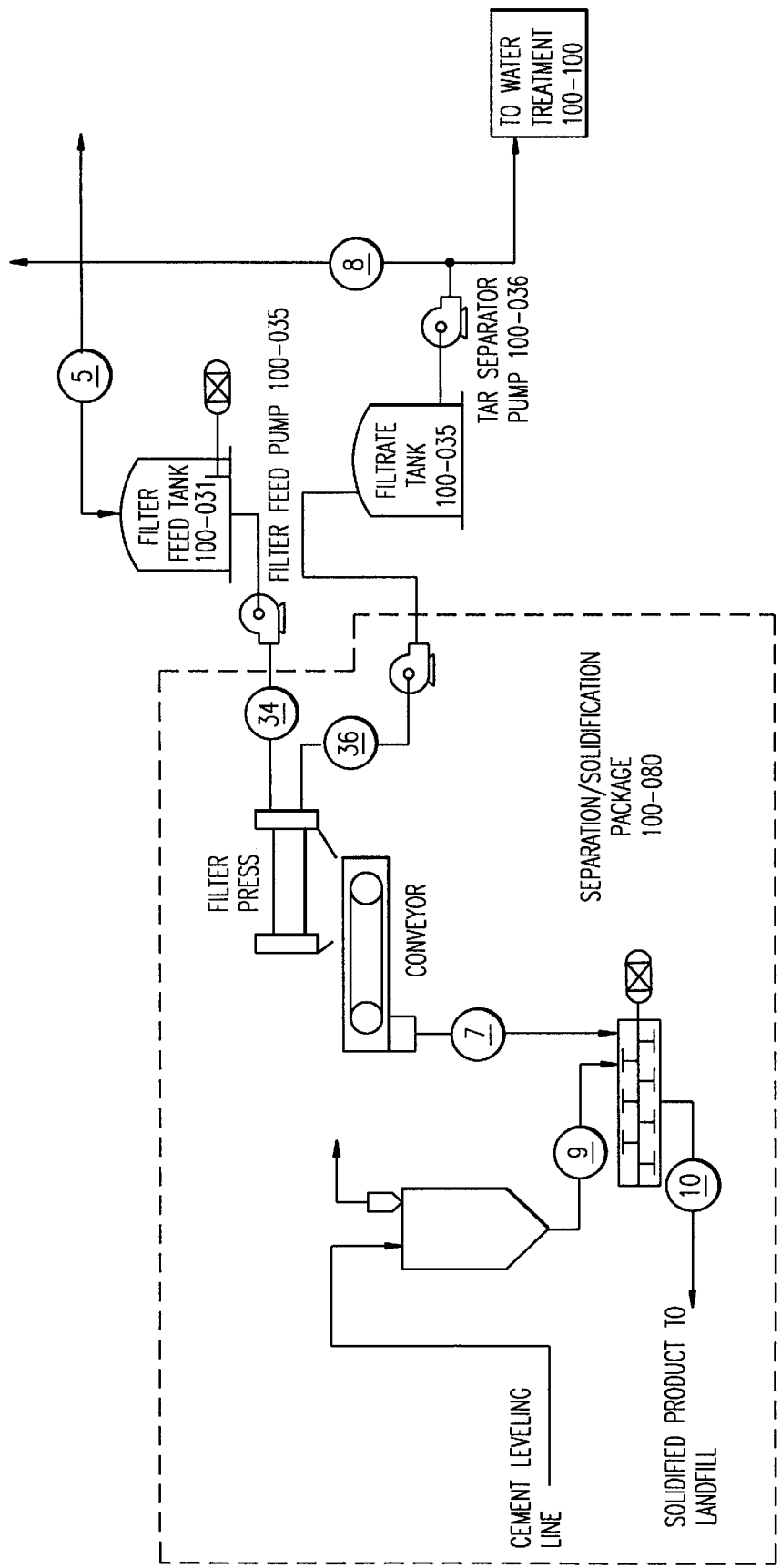

FIG. 1b illustrates a typical reactor set-up which can be used in a batch mode as well as in the modes described below. The neutralized slurry and inoculum are placed in a bioreactor. Air or oxygen may be pumped into the reactor and the contents agitated, mechanically in the bioreactor.

6.3.4.2. Sequencing Batch Mode Operation

Sequencing batch mode is operated much the same as batch mode except that after the incubation period is over, the reactor is allowed to settle for a time, usually about 15 minutes, and the top 60%–95% of the reactor contents are removed, leaving settled solids at the bottom as inoculum for the next batch of neutralized slurry. Preferably between 70% and 90% of the contents are drawn off. Sequencing batch mode is a preferred embodiment for slurry phase aerobic degradation because the lag or acclimation phase is reduced, high levels of biomass are retained in the reactor, variability in the composition of the waste feed is better accommodated, and the residual solids remaining after biotreatment are potentially reduced.

By using residual solids as the source of inoculum for subsequent runs in both the sequencing batch and batch modes and by using the residual liquid or filtrate to prepare fresh slurry, the process operates on a net loss of water. Therefore, this results in no aqueous effluent being produced.

6.3.4.3. Semi-Continuous Mode

Semi-continuous mode is similar to both batch and sequencing batch modes. However, rather than stopping the incubation after a predetermined time, fresh slurry is pumped into the bioreactor in a fixed amount over a given period of time as treated slurry is drawn out of the bioreactor. This provides for a continuous treatment of slurry without having to stop the biodegradative process.

6.4. Solid Phase Degradation

Another embodiment of the present invention is directed to methods for solid phase aerobic degradation of materials. This embodiment involves methods for the treatment of solids, sludges, including those which are tarry and/or elastomeric in nature, as well as soils, sediments, and sorptive materials, including but not limited to granulated activated carbon, said materials containing least one compound or mixture of at least two compounds selected from the group consisting of aromatic, nitro-aromatic, halo-aromatic, halo-nitro-aromatic, aliphatic and halo-aliphatic compounds.

6.4.1. Solid Phase Methods and Biotreatment Parameters

The methods for solid phase bioremediation of solids, sludges or soils containing at least one compound or a mixture of at least two compounds selected from the group consisting of aromatic, nitro-aromatic, halo-aromatic, halo-nitro-aromatic, aliphatic and halo-aliphatic compounds comprise (a) mixing said solid, sludge or soil with a bulking agent such that air can readily pass through the bulked mixture; (b) adjusting the pH of the bulked mixture towards neutrality, if necessary; and (c) contacting said bulked mixture with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. The methods can further comprise culturing said microorganisms with said bulked solid, sludge or soil such that said compound is degraded to products comprising $CO_2$ and $H_2O$. In one embodiment, the compound contained in the solid, sludge, soil or other waste material is selected from benzene, toluene, xylene, ethylbenzene, naphthalene, chlorobenzene, phenol, cresol, nitrobenzene, aniline, anthracene, dimethylphenol, styrene, halonaphthalene, 2-, 3- or 4-chlorotoluene, 2-, 3- or 4-chlorobenzoate, 1,3-dichlorobenzoate, 1,2-, 1,3- or 1,4-dinitrobenzene, 1-chloro-3-nitrobenzene, 1-chloro-4-nitrobenzene, 1- or 2-methylnaphthalene, pyrene, acenaphthylene, fluoranthene, phenanthrene, benzo-(b)-fluoranthene, dibenzofuran, chrysene, catechol, m-toluic acid, cinnamyl acetate, vanillin, trans-cinnamaldehyde, mesitylene, salicylate, melamine, and cyanuric acid or a mixture of said compounds. In another embodiment, the compound contained in the solid, sludge or soil is selected from methanol, formaldehyde, chloroform, $\delta$-(-)-limonene, and hexadecane or a mixture of said compounds.

Where the solid, sludge or soil is a tarry or elastomeric solid, sludge or soil containing at least one compound or a mixture of compounds selected from the group consisting of aromatic, nitro-aromatic, halo-aromatic, halo-nitro-aromatic, aliphatic and halo-aliphatic compounds, the methods for solid phase bioremediation comprise: (a) mixing a tarry or elastomeric solid, a tarry or elastomeric sludge or a tarry or elastomeric soil with a detackifying agent such that said solid soil or sludge forms a particularized mixture which is less tarry and/or elastomeric; (b) adjusting the pH of said mixture towards neutrality, if necessary; and (c) contacting said mixture with microorganisms, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. The methods can further comprise combining the particularized tarry or elastomeric solid, tarry or elastomeric sludge or tarry or elastomeric soil with a bulking agent either simultaneously with or following step (a).

Suitable detackifying agents are selected from clays, chopped, minced or otherwise finely divided organic materials, powdered inorganic salts and rock dust. Alternatively, detackifying agents are selected from pulverized lime, portland cement, bentonite clay, sawdust, diatomaceous earth, pulverized corn cobs and mixtures thereof.

Suitable bulking agents are selected from the group consisting of chopped, minced or otherwise finely divided organic materials and inorganic salts. More specifically, the bulking agents are selected from the group consisting of wood chips, sawdust, corn cobs and mixtures thereof.

According to a preferred embodiment, the bulking agent can also serve as a detackifying agent, for example, including but not limited to wood chips, sawdust, corn cobs and mixtures thereof.

6.4.2. Microorganisms/Inoculum For Solid Phase Degradation

A pure culture of microorganisms or a mixed culture of microorganisms selected from those described in Section 6.1 above are used as inoculum for the solid phase method. The microorganisms used are selected based on their ability to degrade a desired compound or mixture of compounds present in a particular solid aerobically.

The microorganisms are induced as described in Section 6.1 above by growing them, for example, on a medium, which contains as the sole source of nutrients the compound (s) one wishes to degrade.

Alternatively, residual solids from a previously performed solid phase bioremediation, which contains already induced microorganisms, can be used as inoculum for the solid phase method. For example, after a pile of solids has been bioremediated, it contains already induced microorganisms, which can be added to another pile to be bioremediated.

If a bioremediated pile is not available, the inoculum can be re-established by using preserved cultures of the microorganisms described in Section 6.1.1 through 6.1.4 to inoculate several plates per preserved culture. The plates containing Stanier's minimal medium supplemented with appropriate hydrocarbon(s) are then incubated at 25° C. When the cultures have grown, the plates are washed with 5–10 ml of Stanier's minimal medium. The washes are pooled and used to inoculate a series of biphasic flasks with medium supplemented with agar and the appropriate hydrocarbon(s), and 50 ml of liquid medium of the same composition. After the microorganism inoculated in the biphasic flasks has grown-up, the surface of the agar layer is scraped to remove cells. The liquid layer from 4 flasks can be used to inoculate a pile. This can be scaled up to any size required as described above in Section 6.3.2.

6.4.3 Treatment of Solids

After the bulked, neutralized, and inoculated solid is placed in a composting-like pile bioreactor or vessel, it is incubated for a predetermined time, during which, for example, oxygen or air or a mixture thereof is passed through the material to ensure aerobic degradation of the compound(s). The solid material may be mixed occasionally, but this is contraindicated for solids that have a high level of volatile compounds. Further, as described above, the solids may be removed from the pile bioreactor or vessel and extracted, for example, with methylene chloride:methanol, (90:10), to measure the concentration of selected compound(s) by gas-liquid chromatography or by the TCLP procedure.

6.5. Biofilters

Another embodiment of the present invention is a biofilter and methods for its use. Biofilters are used in the bioremediation of compounds in effluents such as air, vapors, aerosols, and water or aqueous solutions.

The biofilters of the present invention comprise an apparatus having microorganisms immobilized on a solid support, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. Suitable solid supports include but are not limited to, granular activated carbon, wood chips, alumina, ruthenium, iron oxide, ceramic or alginate. The apparatus can have influx and efflux orifices, such that the material to be treated can flow through the apparatus.

The biofilters can be used, for example, for bioremediation of an effluent containing a compound selected from the group consisting of aromatic, nitro-aromatic, halo-aromatic, halo-nitro-aromatic, aliphatic and halo-aliphatic compounds. The method comprises flowing said effluent through a biofilter which comprises an apparatus having microorganisms immobilized on a solid support, said microorganisms being a member of the group consisting of microorganisms having ATCC Accession No. 55644, 55648, 55645, 55641, 55647, 55642, 55643, 55646, 55649, 55722, 55723, 55726, 55727, 55724, and 55725. The method may further comprise monitoring the effluent to determine that the compound(s) have indeed been degraded.

6.6. Two-Step Process For Degradation

According to yet another embodiment of the invention, a two step method for aerobic degradation of waste materials containing at least one compound, selected from heavily halogenated organic compounds such as polychlorinated biphenyls, polybrominated biphenyls, etc., heavily nitrated organic compounds, such as trinitrotoluene, etc., and heavily nitrated and cross-linked polymeric compounds, e.g., nitrocellulose, etc. is provided. The waste materials can further comprise a compound selected from the group consisting of aromatic, nitro-aromatic, halo-aromatic, halo-nitro-aromatic, aliphatic and halo-aliphatic compounds or a mixture of such compounds. The methods comprise: (a) combining a reagent capable of chemically degrading, at least partially, a heavily halogenated, a heavily nitrated or a heavily nitrated cross-linked compound in a waste material to form a pretreated composition; and (b) contacting said pretreated composition with microorganisms, said microorganisms being a member of the group consisting of microorganisms having ATCC Accession No. 20 55644, 55648, 55645, 55641, 55647, 55642, 55643, 55646, 55649, 55722, 55723, 55726, 55727, 55724, and 55725. The method can further comprise culturing the microorganisms such that at least one said compound is degraded to products comprising $CO_2$ and $H_2O$. According to one mode of this embodiment, waste materials containing at least one compound or a mixture of compounds selected from the group consisting of benzene, toluene, xylene, ethylbenzene, naphthalene, chlorobenzene, phenol, cresol, nitrobenzene, aniline, anthracene, dimethylphenol, styrene, halonaphthalene, 2-, 3- or 4-chlorotoluene, 2-, 3- or 4-chlorobenzoate, 1,3-dichlorobenzoate, 1,2-, 1,3- or 1,4-dinitrobenzene, 1-chloro-3-nitrobenzene, 1-chloro-4-nitrobenzene, 1- or 2-methylnaphthalene, pyrene, acenaphthylene, fluoranthene, phenanthrene, benzo-(b)-fluoranthene, dibenzofuran, chrysene, catechol, m-toluic acid, cinnamyl acetate, vanillin, trans-cinnamaldehyde, mesitylene, salicylate, melamine, cyanuric acid, methanol, formaldehyde, chloroform, $\delta$-(-)-limonene, and hexadecane are degraded. The reagent can be, but is not limited to, Fenton's reagent, which is a mixture of ferrous sulfate and hydrogen peroxide. Other examples include, but are not limited to free radicals, UV light, metallic iron, peroxidase enzymes such as lignin and lignin-like enzymes. These reagents partially degrade a recalcitrant compound(s) to a compound which the microorganisms can degrade, such that the microorganisms can now finish the degradation of the compound(s).

7. Example: Storage and Induction of Microorganisms

Mixed cultures of the isolated microorganisms were maintained on 1.5–2.0 ml of BACTO™ R2A medium (Difco, Detroit, Mich.) in 4.0 ml Wheaton vials. Cultures inoculated onto the maintenance medium were incubated at 25°–27° C. for 48 hours. After this incubation the cultures were wrapped with parafilm and stored at 4° C.

In one set of experiments, the mixed culture was induced by returning the stored culture to ambient temperature and transferring the mixed culture to 1% agar bacterial plates with fresh BACTO™ R2A medium supplemented with 1000–4000 ppm naphthalene, 30–300 ppm nitrobenzene, 400–500 ppm benzene, 400–500 ppm toluene, 400–500 ppm xylenes, 30–300 ppm aniline, 400-500 ppm ethylbenzene, 50-300 ppm chlorobenzene, 200 ppm 2-methylnaphthalene and about 200 ppm 2-chloronaphthalene. The plates were incubated for 48–96 hours at 25°–27° C. The cultures were then transferred to bacterial plates with Stanier's minimal medium (Stanier et al., 1966, J. Gen. Microbiol. 43:159–271) supplemented with the same hydrocarbon compounds as listed above and incubated for an additional 48 hours at 25°–27° C. After incubation, the plates were washed with 5–10 ml Stanier's minimal medium, the washes pooled and used to incubate biphasic flasks. The biphasic flasks contained 75 ml of Stanier's minimal medium (liquid) in the upper layer and 50 ml of Stanier's minimal medium with 2% agar. Both the upper layer and the lower layer were supplemented with the hydrocarbons listed above. The flasks were incubated at 25°–27° C. for 48–96 hours. The cells, now induced, were scraped off the surface of the agar and used as inoculum.

In another set of experiments, the mixed culture is induced by returning the stored culture to ambient temperature and transferring the mixed culture to 0.3% agar bacterial plates with fresh BACTO™ R2A medium supplemented with 1000–4000 ppm naphthalene, 30–300 ppm nitrobenzene, 400–500 ppm benzene, 400–500 ppm toluene, 400–500 ppm xylenes, 30–300 ppm aniline, 400–500 ppm ethylbenzene, 50–300 ppm chlorobenzene, 200 ppm 2-methylnaphthalene and about 200 ppm 2-chloronaphthalene. The plates are incubated for 48–96 hours at 25°–27° C. The cultures are then transferred to bacterial plates with Stanier's minimal medium (Stanier et al., 1966, J. Gen. Microbiol. 43:159–271) supplemented with the same hydrocarbon compounds as listed above and incubated for an additional 48 hours at 25°–27° C. After incubation, the plates are washed with 5–10 ml Stanier's minimal medium, the washes pooled and used to incubate biphasic flasks. The biphasic flasks contained 75 ml of Stanier's minimal medium (liquid) in the upper layer and 50 ml of Stanier's minimal medium with 2% agar. Both the upper layer and the lower layer are supplemented with the hydrocarbons listed above. The flasks are incubated at 25°–27° C. for 48–96 hours. The cells, now induced, are scraped off the surface of the agar and used as inoculum.

8. Example: Slurry Phase Degradation

8.1 Example: Batch Mode Degradation

An elastomeric sludge containing a mixture of high levels of aromatic, nitro-aromatic, halo-aromatic, halo-nitro-aromatic, aliphatic and halo aliphatic compounds was fluidized as described in Section 6.3 above, by mixing the elastomeric sludge with water.

Table 9 shows the average concentration in ppm for selected compounds found in the original elastomeric sludge.

TABLE 9

| COMPOUND | (Average concentration in ppm) |
|---|---|
| Chloroform | 680 |

TABLE 9-continued

| COMPOUND | (Average concentration in ppm) |
|---|---|
| Benzene | 720 |
| Toluene | 3,000 |
| Chlorobenzene | 130 |
| Ethylbenzene | 240 |
| o-xylene | 680 |
| Aniline | 630 |
| Nitrobenzene | 720 |
| Naphthalene | 42,000 |
| 2-Methylnaphthalene | 2,800 |
| 2-Chloronaphthalene | <100 |
| m,p-xylene | 2,300 |

After mixing, the slurry was decanted away from residual elastomeric sludge to form an approximately 30% (w/w) slurry and into a conventional stirred tank vessel (B. Braun, Allentown, Pa.). The slurry was neutralized to approximately pH 7 by the addition of NaOH (2N) and inoculated with a 10% (v/v) mixed culture of induced microorganisms. These hydrocarbon compounds present in the elastomeric sludge were the only source of carbon and energy for the microorganisms.

A 4 liter vessel containing the inoculated neutralized slurry was stirred at about 200–700 rpm, preferably 400 rpm, and aerated with pure oxygen at about 15 Psi, 250 ml/min at room temperature for 24 hours. The slurry was sampled before and after biological treatment of 24 hours to determine the concentration of compounds present in the slurry. The slurry was extracted using the Toxicity Characteristic Leaching Protocol, (TCLP), and analyzed by gas-liquid chromatography as outlined by EPA SW-846. As seen in Table 10, the compounds present in slurry that were analyzed were successfully bioremediated.

TABLE 10

30% Percent Slurry

| Compound | TCL Untreated* | TCLP Treated* | TCLP Limits |
|---|---|---|---|
| Chloroform | 314 | <1 | 6.0 |
| Benzene | 94 | <0.5 | 0.5 |
| Toluene | 509 | <1 | *** |
| Chlorobenzene | 18 | <1 | 100.00 |
| Ethylbenzene | 15 | <0.5 | *** |
| o-Xylene | 61 | <0.5 | *** |
| Aniline | 114 | <1 | *** |
| Nitrobenzene | 39 | <1 | 2.0 |
| Naphthalene | 3249 | <5 | *** |

*Concentrations in ppm
***TCLP Limits not yet established.

Effluent gas, containing stripped VOC and $CO_2$ was collected in two granular activated carbon traps and in two alkali (2N KOH) traps, respectively. Over the 24 hour incubation period, less than 2% of the total volatile organic compounds present were lost due to stripping.

Figure 3:
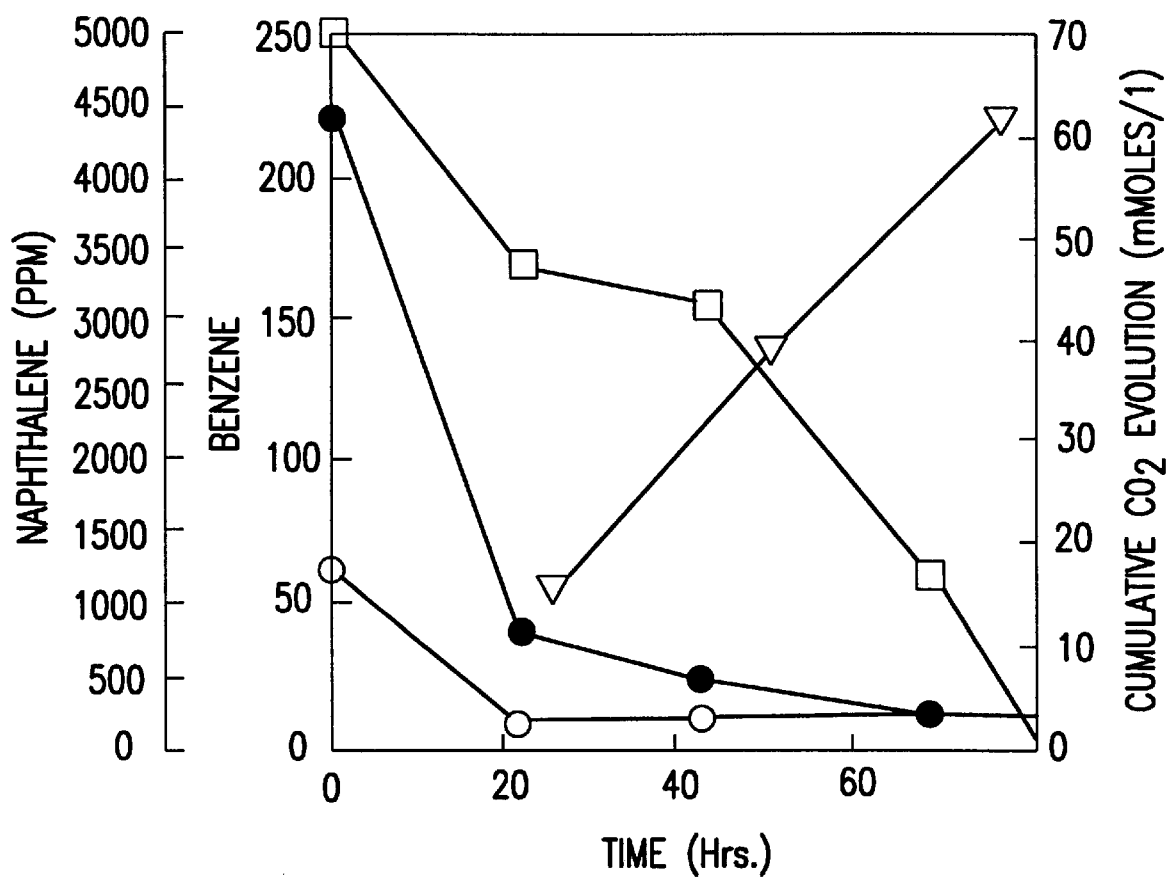
FIG. 3. A graph demonstrating the correlation between decreasing levels of hydrocarbon compounds and increasing levels of $CO_2$ evolved. □ Naphthalene; ● Toluene; ○ Benzene; ∇ $CO_2$.

Further, FIG. 3 shows a correlation between decreasing amounts of compounds present and an increasing amount of $CO_2$ produced by the microorganisms. Because the vessel was aerated with pure oxygen, any $CO_2$ production was a direct result of microbial aerobic utilization of the compounds present in the slurry. Therefore, FIG. 3 also indicates that the microorganisms were able to utilize the compounds present in the original sludge as the sole source of carbon and energy and that these compounds were degraded to products comprising $CO_2$ and $H_2O$.

8.2 Sequencing Batch Mode Degradation: Example 1

The same elastomeric sludge used in Section 8.1 was fluidized, neutralized and inoculated in the same manner with a mixed culture inoculum. However, rather than stopping the degradation of the compounds every 24 hours to empty and completely re-fill the vessel for a new round of bioremediation, only part of the contents of the reactor was emptied. For a 30 day period, after each 24 hour incubation, except over weekends, the contents of the vessel were allowed to settle for 15 minutes. Once the solids contents of the vessel settled, 80% of bioremediated slurry was removed from the top of the vessel. An equal amount of a fresh non-bioremediated 30% slurry (w/w) from the same original source was added into the vessel. The vessel contents were then stirred and aerated with pure oxygen for another 24 hours as described in Section 8.1.

Figure 4:
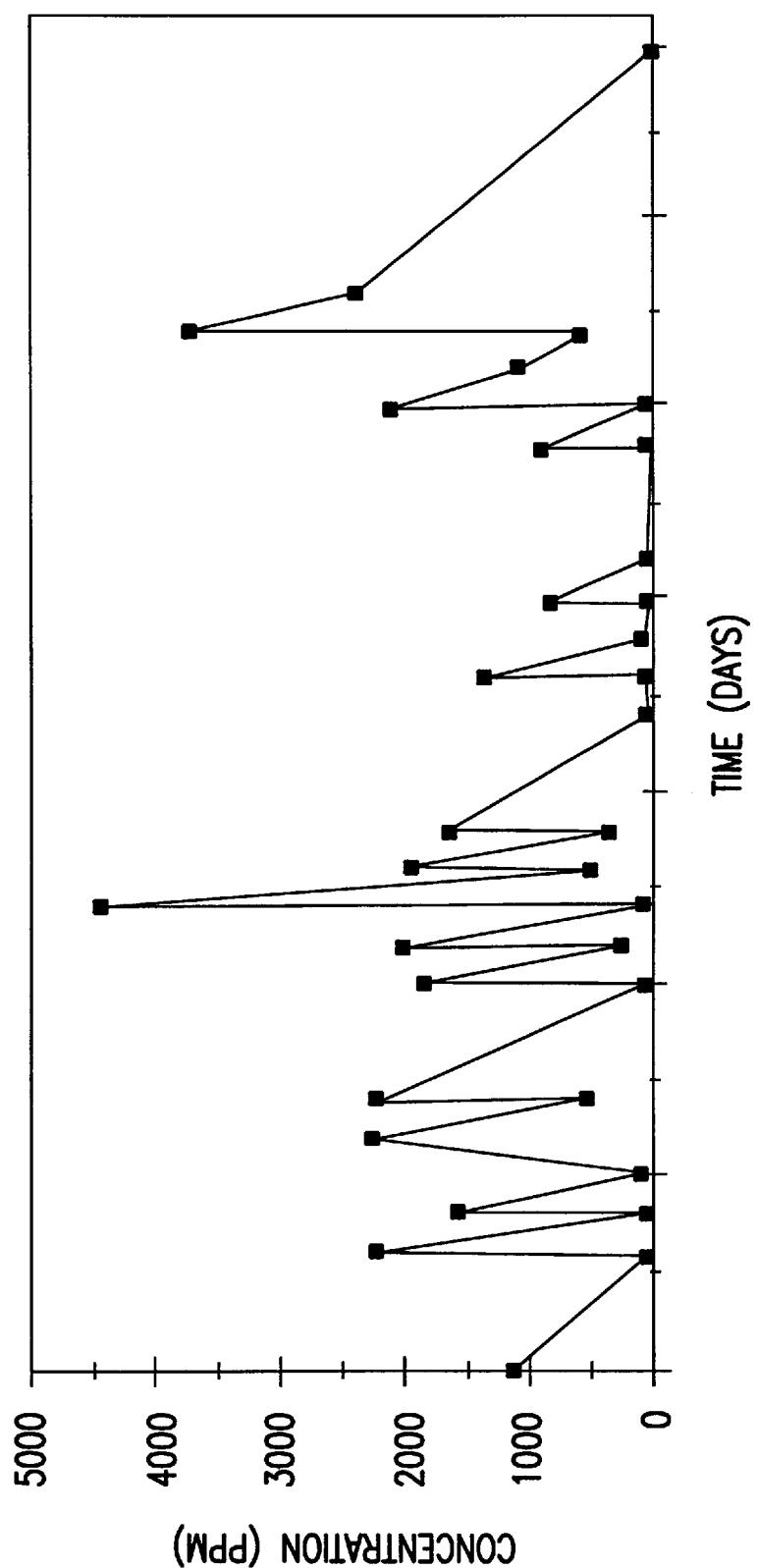
FIG. 4. A graph demonstrating naphthalene degradation over 30 days in a sequencing batch bioreactor. ■ Naphthalene.

40 ml samples of the vessel contents were taken before and after each 24 hour incubation period, extracted with methylene chloride: methanol (90:10) and analyzed for naphthalene by gas-liquid chromatography as described in Section 8.1. FIG. 4 demonstrates that aerobic degradation of naphthalene using the sequencing batch mode over a period of 30 days was rapid and consistent, that the microorganisms present tolerated large variation of naphthalene, 700 ppm to 4,700 ppm, and that these large variations had little or no effect on the ability of the microorganism to aerobically utilize naphthalene and degrade it to products comprising $CO_2$ and $H_2O$.

8.3 Sequencing Batch Mode Degradation: Example 2

A non-elastomeric solid was fluidized with water to form a 30% (w/w) slurry. Table 11 shows the concentration of various selected compounds found in the original solid in parts per million (ppm).

TABLE 11

| COMPOUND | Range of Concentration (ppm) |
|---|---|
| Chloroform | <10 |
| Benzene | 2005–2284 |
| Toluene | 38–42 |
| Chlorobenzene | 1914–2112 |
| Ethylbenzene | 521–578 |
| o-xylene | 803–887 |
| Aniline | 301–331 |
| Nitrobenzene | 321–256 |
| Naphthalene | 37–40 |
| 2-Methylnaphthalene | 654–729 |
| 2-Chloronaphthalene | <10 |
| m,p-xylene | 2126–2362 |

Figure 5:
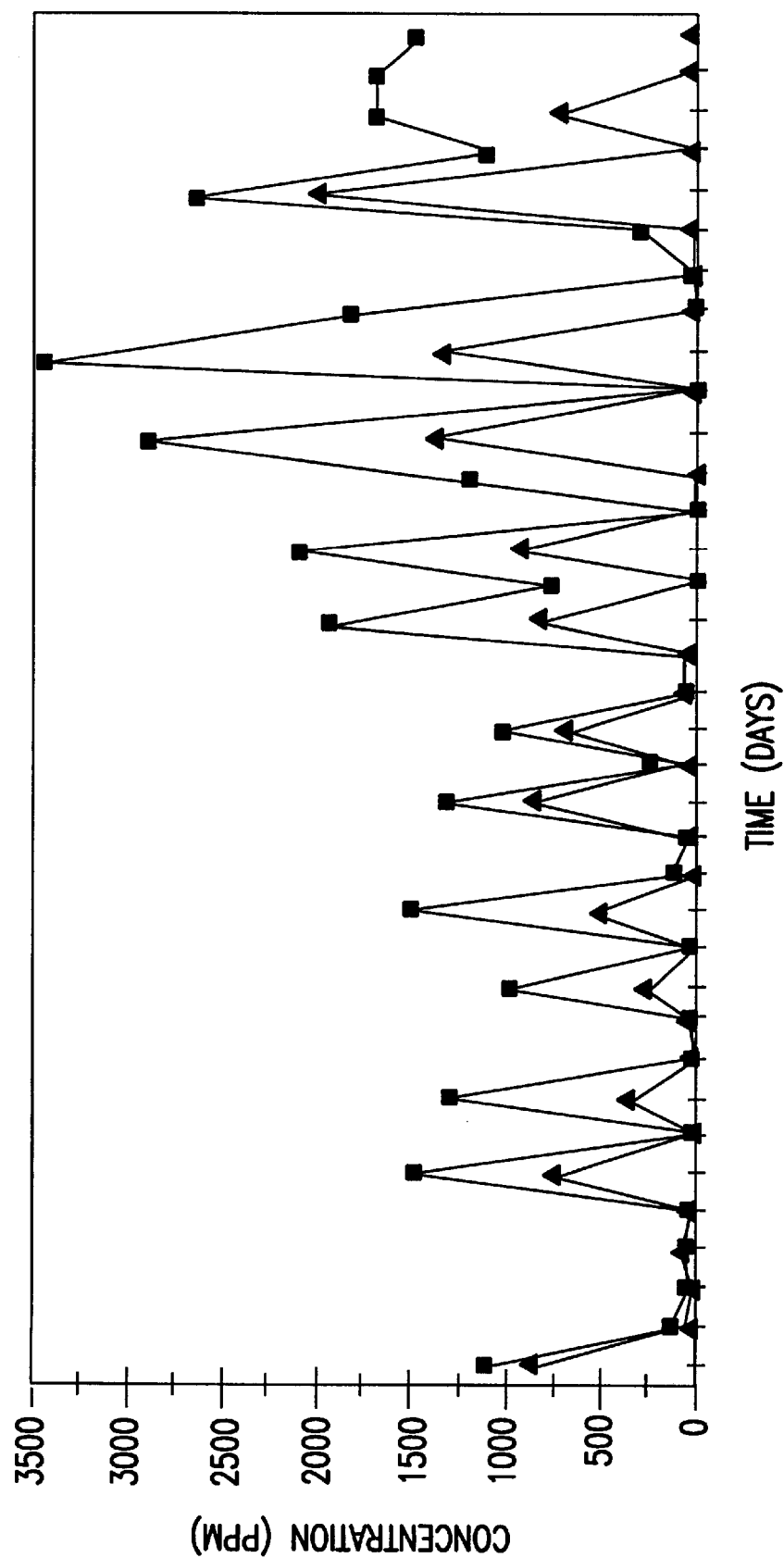
FIG. 5. A graph demonstrating naphthalene and benzene degradation over 30 days in a sequencing batch bioreactor. ■ Naphthalene; ▲ Benzene.

The 30% (w/w) slurry produced had an alkaline pH and was neutralized with a 30% (w/w) slurry with an acidic pH produced from the elastomeric sludge of Section 8.1 in an 1:1 ratio. Subsequently, 2N $H_2SO_4$ acid was added to pH the combined mixture of the two slurries to neutrality. A mixed culture of induced microorganisms 5–20% (w/v), preferably about 10% was added to the neutralized slurry and the mixture was stirred and aerated with pure oxygen for 24 hours. After incubation, the contents were allowed to settle for 15 minutes and then 80% of the contents were drawn off the top. Fresh neutralized slurry produced as described above was added back and the vessel contents were again stirred and aerated. A sample of the vessel contents was removed before and after each 24 hour incubation and analyzed for benzene and naphthalene. FIG. 5 shows the successful bioremediation of benzene and naphthalene present in the slurry over 30 days.

8.4 Example: Batch Mode Degradation

A 30% (w/w) neutralized slurry produced from an elastomeric sludge and a 33% (w/w) neutralized slurry produced from another elastomeric sludge were mixed in a 1:1 ratio. Table 9, above, and Table 12 show the average concentration in parts per million of some selected compounds in each individual elastomeric sludge.

TABLE 12

| COMPOUND | Average concentration in ppm |
| --- | --- |
| Chloroform | 1,000 |
| Benzene | 68,000 |
| Toluene | 16,000 |
| Chlorobenzene | 200 |
| Ethylbenzene | 670 |
| o-xylene | 1,000 |
| Aniline | 1,500 |
| Nitrobenzene | 1,200 |
| Naphthalene | 16,000 |
| 2-Methylnaphthalene | 1,300 |
| 2-Chloronaphthalene | 150 |
| m,p-xylene | 3,500 |

The slurry mixture was added to a stirred tank vessel and inoculated with an induced mixed culture of microorganisms. The vessel contents were stirred and aerated with pure oxygen at room temperature for 40 hours. Samples of the vessel contents taken before incubation, at 16 hours and at 40 hours were extracted with methylene chloride:methanol (90:10) and analyzed by gas-liquid chromatography as described. Table 13 shows that for the compounds analyzed, the compounds were successfully bioremediated by the microorganisms.

TABLE 13

| Compound | TCL Untreated* | TCL t = 16 hr* | TCL t = 40 hr* |
| --- | --- | --- | --- |
| Benzene | 480 | <10 | <10 |
| Toluene | 190 | 90 | <10 |
| Chlorobenzene | 190 | <10 | <10 |
| Ethylbenzene | <10 | <10 | <10 |
| m,p-Xylene | 100 | 90 | <10 |
| Aniline | 80 | 14 | <10 |
| Nitrobenzene | 40 | 13 | <10 |
| Naphthalene | 5100 | 140 | 50 |
| 2-Methylnaphthalene | 180 | 130 | 30 |

*Concentrations in ppm

9. Example: Composting-Like Solid Phase Degradation

Solid phase degradation can be conducted in a chamber, a constructed pile, a heap or the like.

9.1 Example: Loss of Volatile Organic Compounds

Five individual elastomeric sludges containing a mixture of high concentrations of aromatic, nitro-aromatic, halo-aromatic, halo-nitro-aromatic, aliphatic and halo-aliphatic compounds were bulked individually by mixing in a pug mill with sawdust to determine the potential for losses of volatile organic compounds (VOC) such as, for example, benzene, due to stripping during preparation of the material for aerobic degradation of the compounds in the materials according to the methods of the invention.

The elastomeric sludge and a bulking agent, sawdust, were added to the pug mill. For sludges 1–3 and 5, the bulking agent comprised 20% of the mixture, whereas sludge 4, the bulking agent comprised 25% of the mixture. While mixing, nitrogen gas was passed through the headspace of the pug mill to prevent combustion of any flammable material present. Samples for analysis were taken before and after mixing and the relative amount of benzene and chlorobenzene was determined by gas-liquid chromatography.

TABLE 14

| | % Organic Retained After Pretreatment | |
| --- | --- | --- |
| SOLID MATERIAL | Benzene | Chlorobenzene |
| 1 | 60–90 | 80 |
| 2 | 90 | 100 |
| 3 | 70 | 85 |
| 4 | 75–90 | 80–95 |
| 5 | 5–25 | 60–75 |

As seen in Table 14, for 4 out of the 5 sludges tested the loss of benzene due to stripping was only between 6 and 26%. However, for one sludge tested, the amount of benzene lost was between 70 and 90% of the original amount of benzene present. Chlorobenzene was stripped to a lesser extent overall, but the sludge that lost the most benzene also lost the most chlorobenzene. This sludge was unique in that it had a pH>10.5, whereas the other sludges were more or less acidic. These results demonstrate that the pH of a particular sludge or solid can affect the degree to which volatile organic compounds are lost during handling.

9.2 Composting-Like Solid Phase Degradation: Example 1

A soil containing a mixture of organic compounds such as, for example, benzene, toluene, nitrobenzene, naphthalene, chlorobenzene, chloroform, xylene, aniline and ethylbenzene was mixed in a pug mill with a bulking agent, i.e., sawdust. The 80% soil/20% sawdust mixture was neutralized by the addition of NaOH. The neutralized mixture was placed in a vessel, inoculated with an induced liquid mixed culture of microorganisms, and the mixture was treated for 14 days as a pile. The sealed vessels were operated under vacuum conditions in order to draw air through the mixture. Proper air dispersion through the mixture was effected by means of a network of perforated tubing which was positioned beneath the mixture. The effluent air was passed through two granulated activated carbon (GAC) traps to collect volatile organic compounds (VOC). The moisture content and the air flow were held constant during composting. Samples of the soil before and after composting were taken and extracted with methylene chloride:methanol (90:10) or by TCLP and analyzed by gas-liquid chromatography for selected compounds, for example, benzene and nitrobenzene. Table 15 shows two independent treatments of the same material. The concentration in parts per million of the selected compounds found in the bulked soil before and after composting analyzed by both solvent extraction (methylene chloride:methanol) and TCLP as well as the percentage of VOCs both in the residual material and those stripped and trapped in the GAC traps is shown. Solid phase biotreatment was able to reduce the concentration of the analyzed compounds to TCLP limits.

TABLE 15

SOIL
Conditions: inoculated, 30–45% moisture, 0.25 slpm air flow

| | Compounds in material (solvent extraction)* | | TCLP (acidic aqueous extraction) (mg/L) | Percentage VOC | |
|---|---|---|---|---|---|
| Organic Compounds | Initial (ppm) | Final (ppm) | | % residual in material | % volatilized to GAC |
| Benzene | 21.0 | <10 | <0.5 | — | 64.0 |
| Chlorobenzene | <10 | <10 | <1 | — | — |
| Nitrobenzene | <10 | <10 | <2 | — | — |
| Naphthalene | 736.0 | 17.0 | — | 2.3 | 1.7 |
| Benzene | 47.0 | <10 | <0.5 | — | 33.0 |
| Chlorobenzene | <10 | <10 | <1 | — | — |
| Nitrobenzene | <10 | <10 | <2 | — | — |
| Naphthalene | 1245.0 | 31.0 | — | 2.5 | 0.9 |

*TCL

9.3 Composting-Like Solid Phase Degradation: Example 2

A tarry soil containing a mixture of organic compounds was mixed in a pug mill with a bulking agent, i.e., sawdust. The tarry soil/sawdust mixture (80:20) was neutralized by the addition of NaOH and placed in a vessel. The neutralized mixture was inoculated with an induced liquid mixed culture and the vessel sealed. The mixture was treated and analyzed as described in Section 9.2. Table 16 demonstrates two independent successful biotreatments of the tarry soil. The bulked material was successfully treated for both benzene and chlorobenzene as evaluated by TCLP.

TABLE 16

| | Compounds in material (solvent extraction)* | | TCLP (acidic aqueous extraction) (mg/L) | Percentage VOC | |
|---|---|---|---|---|---|
| Organic Compounds | Initial (ppm) | Final (ppm) | | % residual in material | % volatilized to GAC |
| TARRY SOIL Conditions: inoculated, 30–40% moisture, 0.25 slpm air flow | | | | | |
| Benzene | 4377.0 | <10 | <0.5 | — | 61.0 |
| Chlorobenzene | 6606.0 | 62.0 | <1 | 0.1 | 64.3 |
| Nitrobenzene | 74.0 | 70.0 | <2 | 94.6 | 7.0 |
| Naphthalene | 4075.0 | 3038.0 | 3.0 | 74.6 | 3.0 |
| TARRY SOIL Conditions: inoculated, 30–50% moisture, 0.25 slpm air flow | | | | | |
| Benzene | 4137.0 | <10 | NA** | — | 51.4 |
| Chlorobenzene | 6065.0 | 30.0 | | 0.5 | 63.9 |
| Nitrobenzene | <10 | <10 | — | — | — |
| Naphthalene | 3967.0 | 2533.0 | | 63.9 | 3.9 |

*TCL
**Not Available

A significant percentage of both benzene (63%) and chlorobenzene (35.5%) was rapidly removed by stripping during the first two days of treatment, subsequently removal occurred more slowly. Greater than 40% of the naphthalene was removed during treatment with very little stripping (4%) indicating removal was mainly to due aerobic degradation of the compound by the microorganisms present.

9.4 Composting-Like Solid Phase Degradation: Example 3

A tarry soil was detackified and bulked by mixing the soil in the pug mill with sawdust. This mixture was neutralized with NaOH and placed in a vessel. The mixture was inoculated with an induced liquid mixed culture and the vessel sealed. The inoculated mixture was treated as described in Section 9.2. As shown in Table 17, two successful independent biotreatments of the tarry soil were achieved.

TABLE 17

| | Compounds in material (solvent extraction)* | | TCLP (acidic aqueous extraction) (mg/L) | Percentage VOC | |
|---|---|---|---|---|---|
| Organic Compounds | Initial (ppm) | Final (ppm) | | % residual in material | % volatilized to GAC |
| TARRY SOIL Conditions: inoculated, 40–50% moisture, 0.25 slpm air flow | | | | | |
| Benzene | 25320.0 | <10 | <0.5 | — | 15.1 |
| Chlorobenzene | 77.0 | <10 | <1 | — | 98.6 |
| Nitrobenzene | 104.0 | 47.0 | <2 | 0.5 | 11.3 |
| Naphthalene | 10758.0 | 8206.0 | 5.0 | 76.3 | 3.3 |
| TARRY SOIL Conditions: inoculated, 35–50% moisture, 0.25 slpm air flow | | | | | |
| Benzene | 25000.0 | <10 | <0.5 | — | 13.0 |
| Chlorobenzene | 81.0 | <10 | <1 | — | 63.0 |
| Nitrobenzene | 87.0 | 48.0 | <2 | 55.2 | 13.1 |
| Naphthalene | 10440.0 | 8905.0 | 8.0 | 85.3 | 3.8 |

*TCL

The tarry soil contained a very high concentration of benzene (25,000 ppm) and lesser amounts of chlorobenzene and nitrobenzene. Solid phase biotreatment was able to reduce the concentration of these compounds to TCLP limits. The final benzene concentration was less than 10 ppm. Rapid removal of the compound by the microorganisms occurred in the first 48 hours and removal to TCLP limits was achieved within one week. However, only 20–25% of the naphthalene was removed by the microorganisms after 14 days.

9.5 Composting-Like Solid Phase Degradation: Example 4

An elastomeric sludge was detackified and bulked by mixing the elastomeric sludge and sawdust together in a pug mill. While mixing, nitrogen gas was passed through the headspace to prevent combustion of flammable materials. The bulked and detackified sludge was placed in a vessel and the pH neutralized with the addition of NaOH. The neutralized mixture of sludge and sawdust was inoculated with an induced liquid mixed culture and the vessel sealed. The material was treated as a pile for 14 days as described in Section 9.2. Table 18 shows two successful independent biotreatments of the elastomeric sludge.

TABLE 18

SLUDGE
Conditions: inoculated, 30–50% moisture, 0.25 slpm air flow

| Organic Compounds | Compounds in material (solvent extraction)* | | TCLP (acidic aqueous extraction) (mg/L) | Percentage VOC | |
|---|---|---|---|---|---|
| | Initial (ppm) | Final (ppm) | | % residual in material | % volatilized to GAC |
| Benzene | 99.0 | <10 | <0.5 | — | 93.8 |
| Chlorobenzene | 40.0 | <10 | <1 | — | 56.4 |
| Nitrobenzene | 449.0 | <10 | 2.0 | — | 16.5 |
| Naphthalene | 15341.0 | 84.0 | 1.0 | 0.5 | 1.8 |
| Benzene | 89.0 | <10 | <0.5 | — | 109.0 |
| Chlorobenzene | 38.0 | <10 | <1 | — | 6.5 |
| Nitrobenzene | 454.0 | <10 | <1 | — | 13.9 |
| Naphthalene | 13380.0 | 280.0 | <1 | 2.1 | 1.6 |

*TCL

The elastomeric sludge was successfully treated for benzene and nitrobenzene. The final concentration of both compounds was less than 10 ppm. In addition, naphthalene was degraded to less than 330 ppm from 13,000–15,000 pm initially. However, not all removal of these compounds was due to aerobic bioremediation. More than (90%) of the benzene and approximately (15%) of the nitrobenzene were stripped from the mixture during the first two days. On the other hand, stripping was not a major removal mechanism for naphthalene and chlorobenzene indicating that their removal was due mainly to aerobic degradation of the compound by the microorganism added.

9.6 Composting-Like Solid Phase Degradation: Example 5

A tarry sludge containing a mixture of high levels of benzene, chlorobenzene, nitrobenzene and naphthalene was bulked and made less tarry by mixing the tarry sludge with sawdust (25% w/w). The bulked sludge was neutralized with NaOH and placed in a vessel. The neutralized and bulked sludge was inoculated with a liquid mixed culture of microorganism (2–10% w/v) and the vessel sealed. The mixture of sludge, sawdust and microorganisms was treated as a pile for 14 days. The mixture was successfully treated for removal of the compounds tested. Table 19 demonstrates the successful aerobic bioremediation of benzene, chlorobenzene, nitrobenzene and naphthalene as measured by TCLP. 30–60% of the chlorobenzene and 10–30% of the benzene but less than 17% of the nitrobenzene was lost due to stripping. This indicates that the major removal process for these compounds is by bacterial aerobic degradation of these compounds.

TABLE 19

TARRY SLUDGE
Conditions: inoculated, 30–35% moisture, 0.25 slpm air flow

| Organic Compounds | Compounds in material (solvent extraction)* | | TCLP (acidic aqueous extraction) (mg/L) | Percentage VOC | |
|---|---|---|---|---|---|
| | Initial (ppm) | Final (ppm) | | % residual in material | % volatilized to GAC |
| Benzene | 553.0 | <10 | <0.5 | — | 11.3 |
| Chlorobenzene | 3528.0 | 38.0 | <1 | 1.1 | 80.8 |
| Nitrobenzene | 5752.0 | 85.0 | <2 | 1.5 | 7.8 |
| Naphthalene | 17670.0 | 357.0 | <1 | 2.0 | 3.0 |
| Benzene | 643.0 | <10 | <0.5 | — | 35.2 |
| Chlorobenzene | 3905.0 | 644.0 | <1 | 16.5 | 34.5 |
| Nitrobenzene | 6065.0 | 1587.0 | <2 | 26.2 | 0.5 |
| Naphthalene | 16980.0 | 6110.0 | <1 | 36.0 | 0.2 |

*TCL

9.7 Composting-Like Solid Phase Degradation: Example 6

A non-elastomeric sludge was bulked with sawdust (20% w/w) as described above. The bulked sludge, which had an alkaline pH, was neutralized with $H_2SO_4$. The neutralized and bulked sludge was placed in a vessel, inoculated with a liquid mixed culture and treated for 14 days. Table 20 shows two successful individual biotreatments of the same starting material.

TABLE 20

| Organic Compounds | Compounds in material (solvent extraction)* | | TCLP (acidic aqueous extraction) (mg/L) | Percentage VOC | |
|---|---|---|---|---|---|
| | Initial (ppm) | Final (ppm) | | % residual in material | % volatilized to GAC |
| SLUDGE Conditions: no pH control, no inoculum, 50–55% moisture, 250 slpm air flow | | | | | |
| Benzene | 1972.0 | 61.0 | NA** | 3.1 | 88.3 |
| Chlorobenzene | 29.0 | <10 | | — | 81.4 |
| Nitrobenzene | <10 | <10 | | — | — |
| Naphthalene | <10 | <10 | | — | — |
| SLUDGE Conditions: inoculated, 50–55% moisture, 250 slpm air flow | | | | | |
| Benzene | 2135.0 | 55.0 | NA** | 10.2 | 90.1 |
| Chlorobenzene | 30.0 | <10 | | — | 66.4 |
| Nitrobenzene | <10 | <10 | | — | — |
| Naphthalene | <10 | <10 | | — | — |

*TCL
**Not Available

Significant amounts of both benzene and chlorobenzene were stripped and trapped into the GAC traps. Of the benzene and chlorobenzene stripped, greater than 95% of the benzene and 90% of the chlorobenzene were stripped in the first 48 hours. This rapid removal was followed by a slow reduction over the remaining time.

10. Deposit of Microorganisms

The following microorganisms were deposited on Dec. 13, 1994 with the American Type Culture Collection (ATCC), Rockville, Md., and have been assigned the indicated Accession numbers:

| Microorganism | ATCC Accession No. |
|---|---|
| Pseudomonas sp. (DAP 70) | 55646 |
| Pseudomonas sp. (DAP 111) | 55645 |
| Pseudomonas sp. (DAP 622) | 55648 |
| Pseudomonas sp. (DAP 631) | 55647 |
| Aeromonas sp. (DAP 68) | 55642 |
| Aeromonas sp. (DAP 119) | 55641 |
| Corynebacterium sp. (DAP 66) | 55643 |
| Zoogloea sp. (DAP 73) | 55649 |
| Mixed Culture Microorganisms DAP 2 | 55644 |

The following microorganisms were deposited on Nov. 30, 1995 also with the American Type Culture Collection (ATCC), Rockville, Md., and have been assigned the indicated Accession numbers:

| Microorganism | ATCC Accession No. |
|---|---|
| DAP 623 | 55722 |
| DAP 626 | 55723 |
| DAP 629 | 55726 |
| DAP 632 | 55727 |
| DAP 115 | 55724 |
| DAP 120 | 55725 |

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A method for the aerobic degradation of at least one compound selected from the group consisting of aromatic, nitro-aromatic, halo-aromatic, halo-nitro-aromatic, aliphatic and halo-aliphatic compounds comprising contacting said compound with a microorganism, said microorganism being a member of the group consisting of microorganisms having ATCC Accession Nos. 55722, 55723, 55726, 55727, 55724, and 55725.

2. The method according to claim 1, wherein the compound is degraded to products comprising $CO_2$ and $H_2O$.

3. The method according to claim 1, wherein the compound is an aromatic, nitro-aromatic, halo-aromatic, or halo-nitro-aromatic compound.

4. The method according to claim 1, wherein the compound is benzene, toluene, xylene, ethylbenzene, naphthalene, chlorobenzene, phenol, cresol, nitrobenzene, aniline, anthracene, dimethylphenol, styrene, halonaphthalene, 2-, 3- or 4-chlorotoluene, 2-, 3- or 4-chlorobenzoate, 1,3-dichlorobenzoate, 1,2-, 1,3- or 1,4-dinitrobenzene, 1-chloro-3-nitrobenzene, 1-chloro-4-nitrobenzene, 1- or 2-methylnaphthalene, pyrene, acenaphthylene, fluoranthene, phenanthrene, benzo-(b)-fluoranthene, dibenzofuran, chrysene, catechol, m-toluic acid, cinnamyl acetate, vanillin, trans-cinnamaldehyde, mesitylene, salicylate, melamine, cyanuric acid, δ-(-)-limonene, hexadecane, methanol, formaldehyde, or chloroform.

5. The method according to claim 1, wherein the compound is contacted with a microorganism in a medium at a pH value between 3 and 11.

6. The method according to claim 5, wherein the pH value is between 6 and 8.

7. The method according to claim 1, further comprising supplying oxygen by adding an oxygen containing or oxygen liberating composition.

8. The method according to claim 7, wherein the oxygen containing or liberating composition is selected from the group consisting of air, pure oxygen, peroxide, other peroxy chemicals which liberate oxygen and mixtures thereof.

9. The method according to claim 8, wherein oxygen is supplied such that dissolved oxygen tension is between about 0.1% and 100% of saturation.

10. The method according to claim 9, wherein oxygen is supplied such that dissolved oxygen tension is between about 4% and 80% of saturation.

11. A method for the aerobic degradation of a mixture of at least two compounds selected from the group consisting of aromatic, nitro-aromatic, halo-aromatic, halo-nitro-aromatic, aliphatic and halo-aliphatic compounds comprising contacting said compound with a microorganism, said microorganism being a member of the group consisting of microorganisms having ATCC Accession Nos. 55722, 55723, 55726, 55727, 55724, and 55725.

12. The method according to claim 11, wherein the mixture is degraded to products comprising $CO_2$ and $H_2O$.

13. The method according to claim 11, wherein the mixture comprises at least two compounds selected from aromatic, nitro-aromatic, halo-aromatic, or halo-nitro-aromatic compounds.

14. The method according to claim 11, wherein the mixture comprises at least two compounds selected from benzene, toluene, xylene, ethylbenzene, naphthalene, chlorobenzene, phenol, cresol, nitrobenzene, aniline, anthracene, dimethylphenol, styrene, halonaphthalene, 2-, 3- or 4-chlorotoluene, 2-, 3- or 4-chlorobenzoate, 1,3-dichlorobenzoate, 1,2-, 1,3- or 1,4-dinitrobenzene, 1-chloro-3-nitrobenzene, 1-chloro-4-nitrobenzene, 1- or 2-20 methylnaphthalene, pyrene, acenaphthylene, fluoranthene, phenanthrene, benzo-(b)-fluoranthene, dibenzofuran, chrysene, catechol, m-toluic acid, cinnamyl acetate, vanillin, trans-cinnamaldehyde, mesitylene, salicylate, melamine, cyanuric acid, δ-(-)-limonene, hexadecane, methanol, formaldehyde, and chloroform.

15. The method according to claim 11, wherein the mixture is contacted with a microorganism in a medium at a pH value between 3 and 11.

16. The method according to claim 15, wherein the pH value is between 6 and 8.

17. The method according to claim 11, further comprising supplying oxygen by adding oxygen containing or oxygen liberating composition.

18. The method according to claim 17, wherein the oxygen containing or liberating composition is selected from the group consisting of air, pure oxygen, peroxide, other peroxy chemicals which liberate oxygen and mixtures thereof.

19. The method according to claim 18, wherein oxygen is supplied such that dissolved oxygen tension is between about 0.1% and 100% of saturation.

20. The method according to claim 19, wherein oxygen is supplied such that dissolved oxygen tension is between about 4% and 80% of saturation.

21. A biologically pure culture of microorganisms selected from the following strains:

| Microorganism | ATCC Accession No. |
|---|---|
| DAP 623 | 55722 |
| DAP 626 | 55723 |
| DAP 629 | 55726 |
| DAP 632 | 55727 |
| DAP 115 | 55724 and |
| DAP 120 | 55725. |

* * * * *

UNITED STATES PATENT AND TRADEMARK OFFICE
CERTIFICATE OF CORRECTION

PATENT NO. : 5,773,283
DATED : June 30, 1998
INVENTOR(S) : George E. Pierce

It is certified that error appears in the above-identified patent and that said Letters Patent is hereby corrected as shown below:

Claim 14, column 48, line 42, delete "3-nitrobenzene, 1-chloro-4-nitrobenzene, 1- or 2-20" and insert -- 3-nitrobenzene, 1-chloro-4-nitrobenzene, 1- or 2- --.

Signed and Sealed this

Fifteenth Day of September, 1998

Attest:

BRUCE LEHMAN

Attesting Officer

Commissioner of Patents and Trademarks